(12) United States Patent
Mackiewicz

(10) Patent No.: US 11,324,837 B2
(45) Date of Patent: May 10, 2022

(54) HYBRID MEMBRANE-COATED NANOPARTICLE COMPOSITES AND METHODS OF MAKING AND USING THE SAME

(71) Applicant: Portland State University, Portland, OR (US)

(72) Inventor: Marilyn Mackiewicz, Portland, OR (US)

(73) Assignee: Portland State University, Portland, OR (US)

( * ) Notice: Subject to any disclaimer, the term of this patent is extended or adjusted under 35 U.S.C. 154(b) by 156 days.

(21) Appl. No.: 16/127,013

(22) Filed: Sep. 10, 2018

(65) Prior Publication Data
US 2019/0015526 A1    Jan. 17, 2019

Related U.S. Application Data

(63) Continuation-in-part of application No. PCT/US2017/021880, filed on Mar. 10, 2017.

(60) Provisional application No. 62/307,395, filed on Mar. 11, 2016.

(51) Int. Cl.
| | | |
|---|---|---|
| *A61K 47/69* | (2017.01) | |
| *A61K 49/00* | (2006.01) | |
| *A61P 35/00* | (2006.01) | |
| *A61K 49/04* | (2006.01) | |
| *A61K 49/18* | (2006.01) | |
| *A61K 9/51* | (2006.01) | |
| *B82Y 5/00* | (2011.01) | |

(52) U.S. Cl.
CPC ........ *A61K 47/6911* (2017.08); *A61K 9/5115* (2013.01); *A61K 47/6923* (2017.08); *A61K 47/6929* (2017.08); *A61K 49/0084* (2013.01); *A61K 49/0093* (2013.01); *A61K 49/0428* (2013.01); *A61K 49/1812* (2013.01); *A61K 49/1824* (2013.01); *A61K 49/1839* (2013.01); *A61K 49/1845* (2013.01); *A61P 35/00* (2018.01); *B82Y 5/00* (2013.01)

(58) Field of Classification Search
None
See application file for complete search history.

(56) References Cited

U.S. PATENT DOCUMENTS

2008/0089836 A1*  4/2008  Hainfeld ............ A61K 49/0428
424/1.11

FOREIGN PATENT DOCUMENTS

JP        2013159830 A  *  8/2013

OTHER PUBLICATIONS

Li, Y., et al., "Shape effect in cellular uptake of PEGylated nanoparticles: comparison between sphere, rod, cube and disk", Royal Chem. Soc. pp. 16631-16646 (Year: 2015).*
Shen, Y., et al., "Prodrugs Forming High Drug Loading Multifunctional Nanocapsules for Intracellular Cancer Drug Delivery" JACS, pp. 4259-4265 (Year: 2010).*
Gao, F., et al., "A fluorescence ratiometric nano-pH sensor based ondual-fluorophore-doped silica nanoparticles", Spectrochimica Acta Part A, 517-521 (Year: 2007).*
Huang, H., et al., "Formulation of novel lipid-coated magnetic nanoparticles as the probe for in vivo imaging", J. Biomedical Sci., pp. 1-10 (Year: 2009).*
JP201315983A Translation, accessed from: https://patents.google.com/patent/JP2013159830A/en?q=%22silver+nanoparticle%22+oleic+oleylamine&oq=%22silver+nanoparticle%22++oleic+oleylamine&page=1, accessed on Feb. 14, 2021, pp. 1-19 (Year: 2021).*
Black, J.C., "Development of a Biosensor for Investigating Membrane Curvature Sorting ", University of Denver, pp. 1-131 (Year: 2013).*
Messersmith, R.E., et al., "Using the Localized Surface Plasmon Resonance of Gold Nanoparticles To Monitor Lipid Membrane Assembly and Protein Binding", J Phys. Chem. C, pp. 26725-26733 (Year: 2013).*
Lee, K., et al., "Gold and Silver Nanoparticles in Sensing and Imaging: Sensitivity of Plasmon Response to Size, Shape, and Metal Composition", J. Phys. Chem. B, pp. 19220-19225 (Year: 2006).*
Arvizo et al., "Gold nanoparticles: opportunities and challenges in nanomedicine," *Expert Opinion on Drug Delivery*, 7(6): 753-763, Jun. 30, 2010.
Bloemen et al., "Two-Step Directional Surface Modification of Iron Oxide Nanoparticles with Protected Siloxanes," *ChemPlusChem*, 80(1): 50-53, Sep. 15, 2014.
International Search Report and Written Opinion issued for International Application No. PCT/US2017/021880, dated Jun. 21, 2017.
Mackiewicz et al., "C-Reactive Protein Induced Rearrangement of Phosphatidylcholine on Nanoparticle Mimics of Lipoprotein Particles," *J. Phys. Chem. B*, 114(16): 5556-5562, Apr. 29, 2010.
Messersmith et al., "Binding studies of C-reactive protein to lipid coated nanoparticles utilizing fluorescence techniques," *Abstracts of Papers of the American Chemical Society*, vol. 242, Aug. 31, 2011.
Messersmith et al., "Using the Localized Surface Plasmon Resonance of Gold Nanoparticles to Monitor Lipid Membrane Assembly and Protein Binding," *Journal of Physical Chemistry*, 117(50): 26725-26733, Dec. 19, 2013.

(Continued)

*Primary Examiner* — Michael G. Hartley
*Assistant Examiner* — Lance W Rider
(74) *Attorney, Agent, or Firm* — Klarquist Sparkman, LLP

(57) ABSTRACT

Disclosed herein are embodiments of nanoparticle composites that comprise covalently coupled stabilizing agent molecules that improve stability of the nanoparticle composites and allow for tight packing of lipids and/or membranes. The nanoparticle composites can further comprise inhibition inhibitors and/or lipid components that interact to form a hybrid lipid bilayer membrane around the nanoparticle core. The nanoparticle composites can be coupled to drugs, targeting moieties, and imaging moieties. The nanoparticle composites can be used for in vivo drug deliver, disease diagnosis/treatment, and imaging.

17 Claims, 25 Drawing Sheets

(56) References Cited

OTHER PUBLICATIONS

Mock et al., "Shape effects in plasmon resonance of individual colloidal silver nanoparticles," *The Journal of Chemical Physics*, 116(15): 6755-6759, Apr. 15, 2002.

Murphy et al. "Anisotropic Metal Nanoparticles: Synthesis, Assembly, and Optical Applications" *J. Phys. Chem. B*, 109(29): 13857-13870, Jun. 18, 2005.

Sitaula et al., "Gold nanoparticles become stable to cyanide etch when coated with hybrid lipid bilayers," Chem. Common., No. 26, pp. 3013-3015, May 15, 2008.

\* cited by examiner

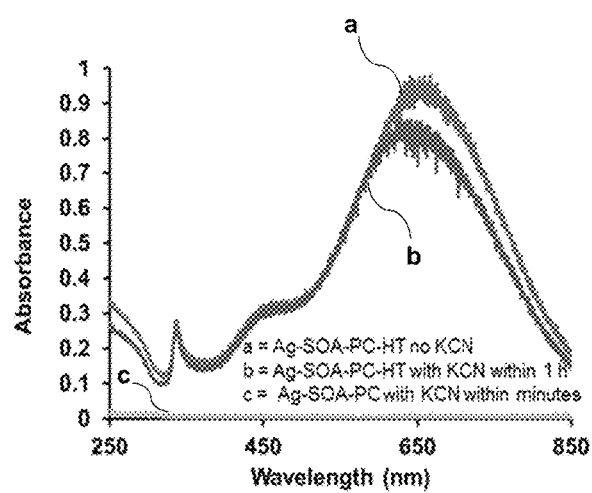 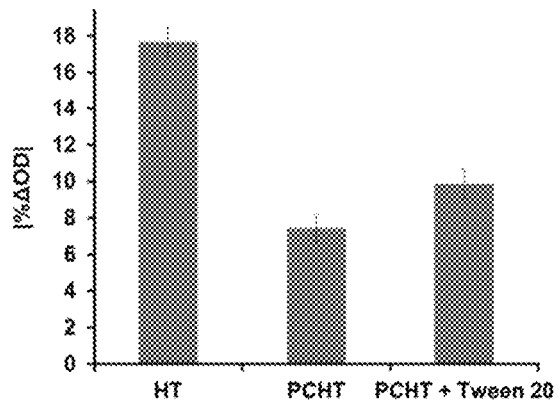
FIG. 26A
FIG. 26B

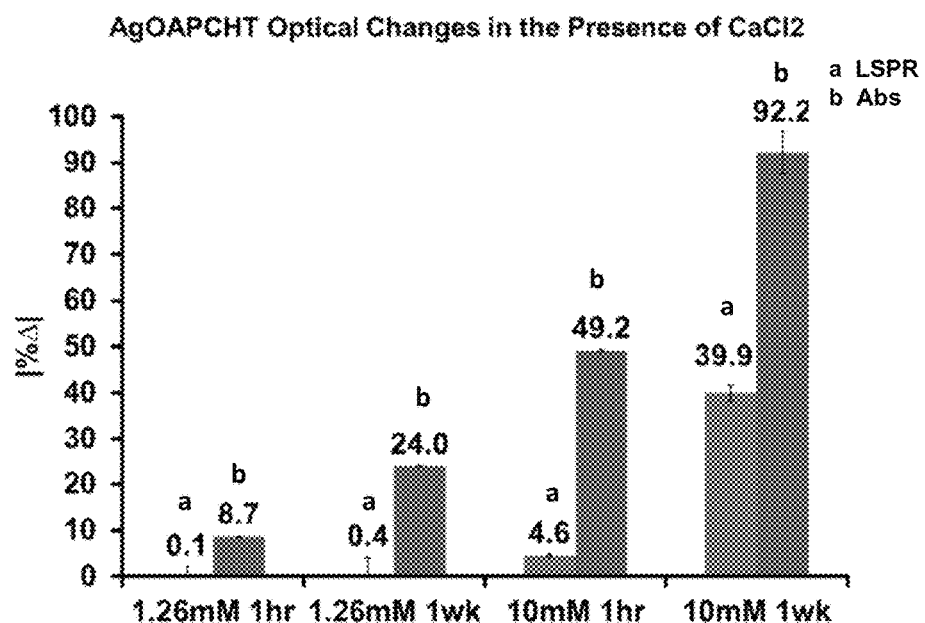
FIG. 28
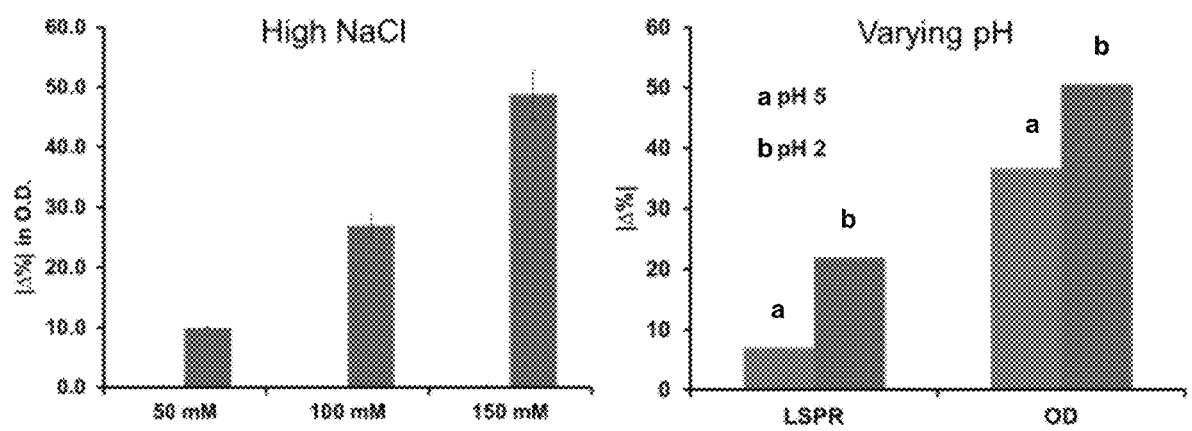
FIG. 29A
FIG. 29B

Preparation of a γAβ conformer Specific Sensors

HYBRID MEMBRANE-COATED NANOPARTICLE COMPOSITES AND METHODS OF MAKING AND USING THE SAME

CROSS REFERENCE TO RELATED APPLICATION

This application is a continuation-in-part under 35 U.S.C. § 120 of International Application No. PCT/US2017/021880, filed on Mar. 10, 2017, which claims priority to and the benefit of earlier filed U.S. Provisional Patent Application No. 62/307,395, filed on Mar. 11, 2016; each of these prior applications is incorporated herein by reference in its entirety.

ACKNOWLEDGMENT OF GOVERNMENT SUPPORT

This invention was made with government support under Contract No. 1762278 awarded by the National Science Foundation. The government has certain rights in the invention.

FIELD

The present disclosure is directed to embodiments of nanoparticle composites and methods of making and using the same.

BACKGROUND

Despite rapid advances in detection and treatment, cancer remains one of the most deadly diseases killing over 1500 Americans each day. Nanotechnological advances show tremendous potential in the area of image-guided drug delivery ("IGDD") development producing platforms that carry imaging agents, drugs, and cancer recognition groups to improve delivery as well as efficacy. However, translational barriers for FDA approval such as in vivo stability, localization in the body and cancer cells, and in vivo toxicity still exist. To overcome these limitations, robust IGDD platforms that incorporate naturally biocompatible ligands, "in use" drugs, or imaging agents that are clinically approved increase the probability of success.

The multi-genic progression of cancer pathology begins with mutations in DNA where normal cells transform into proliferating tumor cells. Common cancer treatment methods for patients include surgery, chemotherapy, radiation, and immunotherapy, which all depend on the location and tumor stage. Chemotherapy is one of the most effective ways of eradicating cancer, however, there are issues with non-specific distribution of drugs to normal and cancer cells, poor solubility, insufficient localization, and multi-drug resistance. These limitations require different tactics for cancer therapy to minimize systematic toxicity. The success rate of new approaches greatly depends on the mechanism of delivery and the selection of an optimal carrier system. While nanotechnological advances have made significant strides in this area, challenges with stability and biocompatibility still require solutions.

Another area of interest is protein membrane interactions, particularly with respect to Alzheimer's research. Both experimental and molecular models have been used to explain Aβ-membrane destabilization and toxicity, as involved in Alzheimer's. While these models have provided answers regarding membrane disruption, many other questions remain. For example, the role of Aβ oligomer size or metals in the conformational state of Aβ with respect to oligomerization, membrane disruption, and lipid peroxidation remains elusive. Therefore, models that allow for studying distinct metal-induced conformational states of Aβ and the effect of oligomer size are needed.

SUMMARY

Disclosed herein are embodiments of nanoparticle composites. In some embodiments, the nanoparticle composites comprise a nanoparticle core and a hybrid lipid bilayer, which can comprise one or more stabilizing agent molecules, one or more lipids, one or more aggregation inhibitor molecules, and combinations thereof. In some embodiments, the stabilizing agent molecules can comprise an aliphatic chain and a heteroatom terminus covalently bound to a surface of the nanoparticle core. Exemplary heteroatoms include, but are not limited to nitrogen, oxygen, or sulfur. In some embodiments, the aggregation inhibitor molecules can comprise a hydrophobic chain and a polar terminus that is not covalently attached to the surface of the nanoparticle core. In an independent embodiment, if the nanoparticle core comprises gold, the stabilizing agent molecule is not, or is other than, propanethiol, hexanethiol, or decanethiol. In some embodiments, the nanoparticle core has a spherical shape, an ellipsoidal shape, a rod-like shape, a cube-like shape, or a triangular shape. In some disclosed embodiments, the nanoparticle core comprises iron oxide or gadolinium oxide and the stabilizing agent molecule comprises one or more oxygen atoms covalently attached to the iron oxide or gadolinium oxide. In some disclosed embodiments, the nanoparticle core comprises silver and the stabilizing agent molecule comprises a nitrogen atom covalently attached to the nanoparticle core. In some embodiments, a plurality of the one or more aggregation inhibitor molecules that form a lipid membrane surrounding the nanoparticle core can also be included.

In some embodiments, the composite further comprises one or more associated drugs, imaging agents, targeting agents, or a combination thereof. The one or more associated drugs can be, but are not limited to, anti-cancer drugs. The imaging agents can be selected from, but are not limited to, chromogens, fluorophores, or mixtures thereof. In yet additional embodiments, the nanoparticle composites themselves act as imaging agents. The targeting agents can be selected from, but are not limited to, cancer biomarkers (or other cell markers), antibodies, peptides, folic acid, sugar moieties, and the like.

Also disclosed herein are embodiments of a methods of making the nanoparticle composites disclosed herein. Such methods can include exposing the nanoparticle core to one or more aggregation inhibitor molecules, exposing the nanoparticle core to the stabilizing agent molecule, and isolating the composite. In particular disclosed embodiments, the method can further comprise pre-determining the number of stabilizing agent molecules to be covalently attached to the nanoparticle core to thereby control the number of aggregation inhibitor molecules needed to substantially cover the nanoparticle core. In some embodiments, the nanoparticle core can be exposed to one or more surfactants to determine membrane integrity.

The foregoing and other objects, features, and advantages of the present disclosure will become more apparent from the following detailed description, which proceeds with reference to the accompanying Appendix and figures.

BRIEF DESCRIPTION OF THE DRAWINGS

FIGS. 26A and 26B show results for a Ag-SOA-PC-HT nanoparticle composite, wherein FIG. 26A shows the UV-Vis spectra of the Ag-SOA-PC-HT nanoparticle composite and a Ag-SOA-PC nanoparticle composite before and after addition of 6 mM KCN; and FIG. 26B shows the % change in the LSPR of the Ag-SOA-PC-HT nanoparticle composite upon addition of Tween®20 and 6 mM KCN.

FIG. 28 is a bar graph comparing the absolute percent change of the UV-spectra LSPR (bars labeled "a") and optical density (bars labeled "b") of Ag-OA-PC-HT composite embodiments exposed to varied concentrations of $CaCl_2$ (1.26 mM and 10 mM), wherein the embodiments were monitored for 1 week, with data collection at 1 hour and 1 week.

FIGS. 29A and 29B show results for a Ag-SOA-PC-HT nanoparticle composite, wherein FIG. 29A shows the change in optical density of the Ag-SOA-PC-HT nanoparticle composite (OD=0.8) after the addition of varying NaCl and FIG. 29B shows the change in optical density and LSPR of the Ag-SOA-PC-HT composite (OD=0.8) after varying pH.

DETAILED DESCRIPTION

I. Overview of Terms

Figure 1:
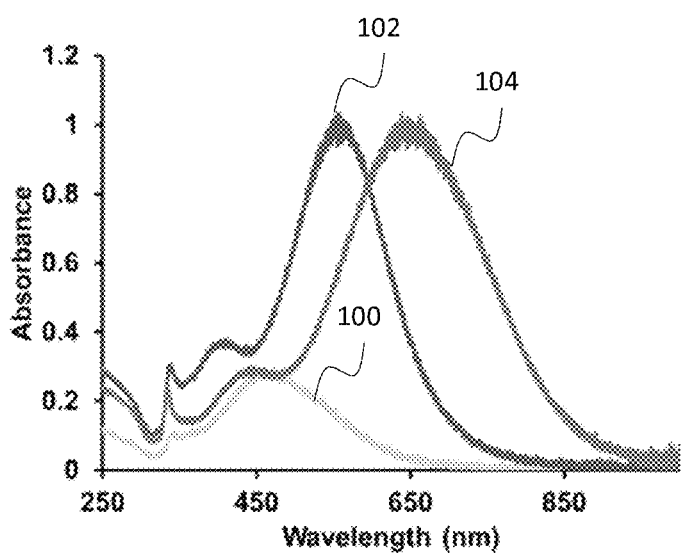
FIG. 1 is a graph of absorbance as a function of wavelength (nm) illustrating that the UV-vis spectra of representative nanoparticle composites disclosed herein can be selectively tuned by selecting a particular shape of a nanoparticle composite disclosed herein.

The following explanations of terms are provided to better describe the present disclosure and to guide those of ordinary skill in the art in the practice of the present disclosure. As used herein, "comprising" means "including" and the singular forms "a" or "an" or "the" include plural references unless the context clearly dictates otherwise. The term "or" refers to a single element of stated alternative elements or a combination of two or more elements, unless the context clearly indicates otherwise.

Unless explained otherwise, all technical and scientific terms used herein have the same meaning as commonly understood to one of ordinary skill in the art to which this disclosure belongs. Although methods and materials similar or equivalent to those described herein can be used in the practice or testing of the present disclosure, suitable methods and materials are described below. The materials, methods, and examples are illustrative only and not intended to be limiting, unless otherwise indicated. Other features of the disclosure are apparent from the following detailed description and the claims.

Unless otherwise indicated, all numbers expressing quantities of components, molecular weights, percentages, temperatures, times, and so forth, as used in the specification or claims are to be understood as being modified by the term "about." Accordingly, unless otherwise indicated, implicitly or explicitly, the numerical parameters set forth are approximations that can depend on the desired properties sought and/or limits of detection under standard test conditions/methods. When directly and explicitly distinguishing embodiments from discussed prior art, the embodiment numbers are not approximates unless the word "about" is recited. Furthermore, not all alternatives recited herein are equivalents.

To facilitate review of the various embodiments of the disclosure, the following explanations of specific terms are provided.

Aliphatic: A hydrocarbon, or a radical thereof, having at least one carbon atom to 50 carbon atoms, such as one to 25 carbon atoms, or one to ten carbon atoms, and which includes alkanes (or alkyl), alkenes (or alkenyl), alkynes (or alkynyl), including cyclic versions thereof, and further including straight- and branched-chain arrangements, and all stereo and position isomers as well.

Alkyl: A saturated monovalent hydrocarbon having at least one carbon atom to 50 carbon atoms, such as one to 25 carbon atoms, or one to ten carbon atoms, wherein the saturated monovalent hydrocarbon can be derived from removing one hydrogen atom from one carbon atom of a parent compound (e.g., alkane). An alkyl group can be branched, straight-chain, or cyclic (e.g., cycloalkyl).

Alkenyl: An unsaturated monovalent hydrocarbon having at least two carbon atoms to 50 carbon atoms, such as two to 25 carbon atoms, or two to ten carbon atoms, and at least one carbon-carbon double bond, wherein the unsaturated monovalent hydrocarbon can be derived from removing one hydrogen atom from one carbon atom of a parent alkene. An alkenyl group can be branched, straight-chain, cyclic (e.g., cylcoalkenyl), cis, or trans (e.g., E or Z).

Alkynyl: An unsaturated monovalent hydrocarbon having at least two carbon atoms to 50 carbon atoms, such as two to 25 carbon atoms, or two to ten carbon atoms and at least one carbon-carbon triple bond, wherein the unsaturated monovalent hydrocarbon can be derived from removing one hydrogen atom from one carbon atom of a parent alkyne. An alkynyl group can be branched, straight-chain, or cyclic (e.g., cycloalkynyl).

Amine: $NP-NHR^b$, or $NP-NR^bR^c$, wherein NP represents the nanoparticle core to which the amine is attached, and each of $R^b$ and $R^c$ independently is selected from aliphatic (e.g., alkyl, alkenyl, alkynyl), aryl, heteroaliphatic (e.g., heteroalkyl, heteroalkenyl, heteroalkynyl), heteroaryl, and any combination thereof.

Aryl: An aromatic carbocyclic group comprising at least five carbon atoms to 15 carbon atoms, such as five to ten carbon atoms, having a single ring or multiple condensed rings, which condensed rings can or may not be aromatic provided that the point of attachment is through an atom of the aromatic aryl group.

Chromogen: A substance capable of conversion to a colored product, such as a pigment or dye. Certain chromogens are electron donors that, when oxidized, become a colored product. Production of a colored product, and the property of becoming insoluble upon chemical conversion, such as by oxidation, make chromogens useful for IHC. Particular examples of chromogenic compounds, without limitation, include diaminobenzidine (DAB), tetramethylbenzidine (TMB), 2,2'-azino-di-[3-ethylbenzothiazoline sulphonate] (ABTS), iodonitrotetrazolium (INT), tetrazolium blue and tetrazolium violet.

Destabilizing Agents: Compounds that degrade nanoparticles cores and/or membrane components surrounding nanoparticle cores. In some embodiments, destabilizing agents can include, but are not limited to, surfactants, salts, acid, bases, ions, and combinations thereof.

Disruptive Ions: Ions that dissociate from a nanoparticle core resulting in nanoparticle core degradation. In some embodiments, disruptive ions can be ions of the metals making up the nanoparticle core from which they dissociate, such as silver ions, gold ions, gadolinium ions, iron ions, and the like. In some embodiments, disruptive ions can have charges ranging from $^{+1}$ to $^{+4}$ (e.g., $Ag^+$ has a $^{+1}$ charge).

Fluorophore: A chemical compound, which when excited by exposure to a particular stimulus, such as a defined wavelength of light, emits light (fluoresces), for example at a different wavelength (such as a longer wavelength of light). Fluorophores are part of the larger class of luminescent compounds. Luminescent compounds include chemiluminescent molecules, which do not require a particular wavelength of light to luminesce, but rather use a chemical source of energy. Therefore, the use of chemiluminescent molecules (such as aequorin) eliminates the need for an external source of electromagnetic radiation, such as a laser.

Heteroaliphatic: A aliphatic group comprising at least one heteroatom to six heteroatoms, such as one to four heteroatoms, which can be selected from, but not limited to oxygen, nitrogen, sulfur, selenium, phosphorous, and oxidized forms thereof within the group.

Heteroaryl: An aryl group comprising at least one heteroatom to six heteroatoms, such as one to four heteroatoms, which can be selected from, but not limited to oxygen, nitrogen, sulfur, selenium, phosphorous, and oxidized forms thereof within the ring. Such heteroaryl groups can have a single ring or multiple condensed rings, wherein the condensed rings may or may not be aromatic and/or contain a heteroatom, provided that the point of attachment is through an atom of the aromatic heteroaryl group.

Hybrid Lipid Bilayer Membrane or Hybrid Membrane: A membrane formed between a layer of lipid molecules (which can have the same or different structure as the disclosed aggregation inhibitors) and a submonolayer comprising aggregation inhibitors and/or stabilizing agent molecules.

Hydrophobic Chain: A straight or branched aliphatic chain. In some embodiments, a hydrophobic chain comprises one or more carbon atoms, with particular embodiments comprising at least two carbon atoms and additional particular embodiments comprising at least six carbon atoms.

Lipid Molecule: A molecule capable of acting as a structural component of a membrane, such as fatty acids, glycerolipids, glycerophospholipids, phospholipids, sphingolipids, saccharolipids, and the like. In some embodiments, lipid molecules of a lipid membrane can be aggregation inhibitors.

Nanomaterial: A material with morphological features and/or special properties derived from its nanoscale dimensions (e.g., having one dimension that is less than 100 nm).

Nanoparticle: A nanoscale particle with a size that is measured in nanometers, for example, a nanoscopic particle that has at least one dimension of less than about 100 nm. Examples of nanoparticles include paramagnetic nanoparticles, superparamagnetic nanoparticles, metal nanoparticles, fullerene-like materials, inorganic nanotubes, dendrimers (such as with covalently attached metal chelates), nanofibers, nanohorns, nano-onions, nanorods, nanoprisms, nanoropes and quantum dots. A nanoparticle can produce a detectable signal, for example, through absorption and/or emission of photons (including radio frequency and visible photons) and plasmon resonance.

Subject: A human or animal subjected to analysis, a treatment, observation, or experiment.

Sugar Residues: Sugar residues can include a monosaccharide, a disaccharide, a polysaccharide, or oligosaccharide moiety, or any derivative thereof.

Thioester Linkage: A functional group having a formula RC(O)SR', wherein R and R' are two molecules, compounds, or functional groups joined together through the thioester linkage.

A person of ordinary skill in the art would recognize that the definitions provided above are not intended to include impermissible substitution patterns (e.g., methyl substituted with 5 different groups, and the like). Such impermissible substitution patterns are easily recognized by a person of ordinary skill in the art. Any functional group disclosed herein and/or defined above can be substituted or unsubstituted, unless otherwise indicated herein.

Abbreviations
LSPR=localized surface plasmon resonance
PT=propanethiol
HT=hexanethiol
PC=phosphatidylcholine
OCT=optical coherence tomography
HBM=hybrid membrane (or hybrid lipid bilayer membrane)
IGDD=image-guided drug delivery
OD=optical density

II. Introduction

Recent nanotechnological advances have provided several drug delivery platforms comprised of nanoparticles, nanotubes, microspheres, dendrimers, and liposomes to overcome challenges in drug delivery. These nanoparticle-based delivery vehicles employ cancer recognition epitopes to target tumors, enhance drug loading, improve biodistribution, and reduce clearance by the reticuloendothelial system (RES). However, while lipid-based nanotechnologies are hallmark IGDD agents, their formulations are susceptible to rearrangement, which reduces their stability so there is uncontrolled release of drugs limiting their efficacy. There are issues with blood circulation times, agglomeration, loading of hydrophilic drugs within the bilayer, and some formulations are not suited for long-term storage. In addition, there are still issues with preparing reproducible and homogenous lipid-based nanoparticles with an embedded imaging agent to visualize uptake and delivery at tumor sites. These are challenges that limit nanotechnological advances in IGDD agents for monitoring cancerous cells at all stages and real-time visualization of drug delivery and response. Consequently, approaches to improve their stability will minimize the uncontrolled release of therapeutics, increase blood circulation levels, and improve targeted delivery of therapeutics. Functionalization of nanocarriers with poly(ethyleneglycol) (PEG) molecules has been utilized in attempts to address these fallbacks. Such PEG-functionalized nanoparticles provide an aqueous shield around the nanocarriers so they are less prone to macrophage recognition and clearance from the body as well as increased stability. However, one drawback of PEG is that it limits contact between membranes and uptake by the cell.

The composites and methods disclosed herein bridge existing gaps in oncological development of IGDD agents through the design of a new class of robust hybrid membrane (HBM)-coated metal nanoparticles. The overarching focus is on the optimization of the lipid-based IGDD design to improve its stability to enhance site-directed delivery, biodistribution, reduce toxicity to normal cells, and for use with a variety of imaging modalities. The technological advancements in the design of HBM-coated AuNPs demonstrate that the present composites can address the limitations of current lipid-based IGDD platforms as discussed herein. The HBM-coated nanoparticle composites described herein can carry and deliver large amounts of therapeutic agents (e.g., cancer therapeutics) and imaging agents, and they have "stealth-like" character because they are similar to natural cellular systems. In addition, both hydrophilic and hydrophobic drugs can be incorporated within the membrane bilayer of the nanoparticle conjugates described herein, and/or can be positioned inside of the nanoparticle composite's aqueous pore, or conjugated to the surface. The disclosed nanoparticle composites may incorporate cancer recognition groups such as RGD peptides, transferrin, or folic acid to improved site-directed delivery of therapeutic drugs to induce cellular death. In addition, the disclosed nanoparticle composites also incorporate imaging agents within the same framework to image cellular uptake and tumor reduction.

Many studies have indicated that small beta amyloid (Aβ) oligomers or conformers (dimers, trimmers, tetramers, etc) are the neurotoxic species involved in AD pathology. While the physiochemical properties of Aβ oligomers or conformers are not well understood, they have been shown to permeate and disrupt membranes, induce oxidative lipid damage, and cause lipid release. Both membrane composition (lipid type, surface charge, and cholesterol content) and metal ions have been shown to influence Aβ oligomerization and interaction with membranes. For example, Aβ binds to membranes with high cholesterol contents that lead to calcium dysregulation in astrocytes and neurons. In addition, metals such as copper ($Cu^{II/III}$), zinc ($Zn^{II}$), iron ($Fe^{II/III}$), and aluminum ($Al^{III}$) also bind to Aβ to form aggregates that disrupt membranes, or undergo redox cycling aerobically in the presence of $Cu^{I/II}$ or $Fe^{II/III}$ and a reducing agent to generate reactive oxygen species (ROS). These effects also lead to neuronal cell death or weakened synaptic cell signaling. Although still controversial, depending on the experimental conditions and type of Aβ species, inhibitory effects have been observed. For example, $Cu^{II}$ ions are known to inhibit aggregation and fibrillation by $Zn^{II}$ ions, while other studies have shown that $Zn^{II}$ plays a pivotal role in attenuating non-toxic plaque formation and is proposed to be neuroprotective. To explain these contradictory results, more controlled studies are required to uncover the important driving mechanisms by which metals play a role in Aβ oligomerization and ROS production. In addition, while membrane models have provided some mechanistic insights regarding how Aβ interacts with membranes many questions still remain. For example, the identity of a specific Aβ conformer or a metallated-Aβ derivative that disrupt membrane interactions remains elusive. In addition, the mechanisms by which metals induce conformational state changes in Aβ that influences its interaction with membranes or cause lipid peroxidation requires elucidation.

In vivo assays have been limited to µMRI and optical fluorescent imaging that rely on late-stage Aβ plaques for diagnosis. Assays that detect biomarkers at early stages of the disease, such as Aβ oligomers are need. While ELISA and other relevant assays have been able to analyze body fluids for Aβ monomers and oligomers, this technique gives one summarized signal for all the Aβ species in a sample. That is, ELISA does not differentiate individual Aβ conformers or metallated-Aβ derivatives that would identify the most relevant Aβ species involved neurotoxicity. To add to the complication, there are four metals associated with AD and it remains unclear which metallated-Aβ species is predominant and induces neurotoxicity. The identity of this species is of significant interest and techniques to detect them are needed. In addition, current technologies are not designed to provide mechanistic insight into the role of Aβ conformer or metallated-Aβ in membrane disruption, lipid peroxidation, and oxidative stress.

Biomimetic models comprised of lipid-coated nanoparticles can serve as investigative probes to elucidate the mechanisms by which Aβ conformers induce membrane disruption and lipid peroxidation in the absence and presence of metals. The localized surface plasmon resonance ("LSPR") of nanoparticles is sensitive to changes in refractive index and the 3D nanoscale structure makes these ideal models and sensors. Disclosed herein are lipid-coated nanoparticles that can be used to investigate the effect of distinct Aβ oligomers on membrane integrity and to determine how metals influence conformational changes to Aβ that drives these Aβ oligomer-membrane interactions as well as lipid peroxidation.

III. Nanoparticle Composites

Figure 2:
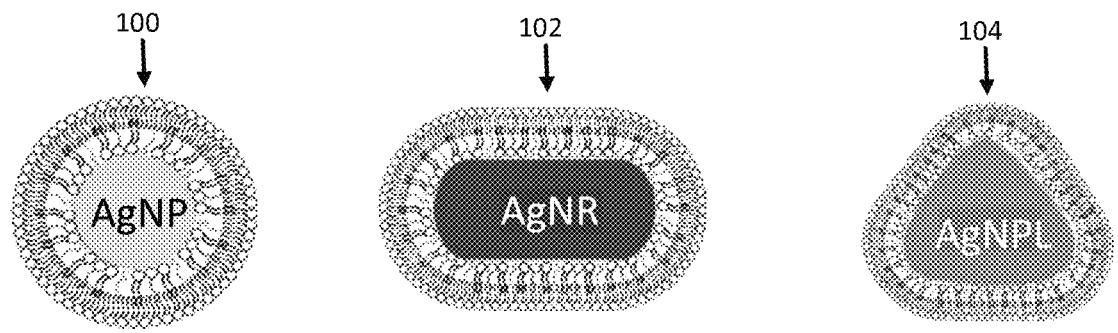
FIG. 2 illustrates different nanoparticle composite embodiments having different shapes that can be selected to tune the optical and electrical properties of hybrid membrane-coated (HBM-coated) nanoparticles.
Figure 3:
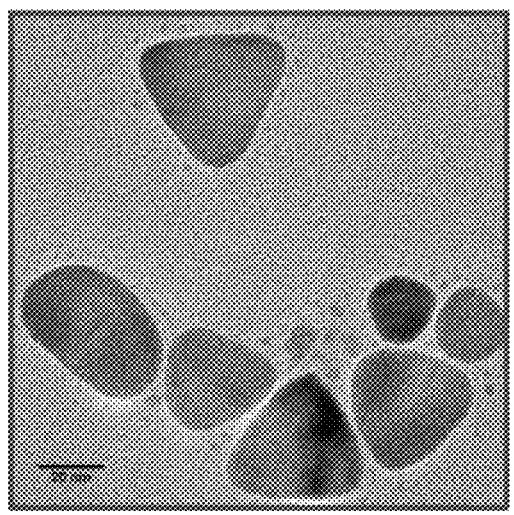
FIG. 3 is a TEM image of representative nanoparticle composites having selected shapes, which can be obtained using nanoparticle synthesis methods described herein.

Disclosed herein are nanoparticle composites, comprising nanoparticle cores that are covalently coupled to one or more stabilizing agent molecules that can be used to form a stabilized hybrid lipid submonolayer that facilitates formation of membrane-coated nanoparticles that are detergent resistant, ion-impermeable, and can serve as robust drug delivery platforms and imaging agents. The nanoparticle composites disclosed herein exhibit improved stability over traditional ligand-functionalized nanoparticles, thereby allowing for longer circulation times in vivo and improved biodistribution for therapeutic applications, such as cancer therapy. For example, the disclosed nanoparticle composites do not undergo lipid rearrangement (e.g., ligand exchange or liposome/micelle rearrangement) or restructuring (e.g., etching, resulting in loss of nanoparticle structure/integrity). The disclosed hybrid lipid bilayer membrane of the nanoparticle composites provides the ability for tight packing of the membrane, thereby protecting the nanoparticle core from oxidants and destabilizing molecules and/or ions for extended periods of time. Due to the covalent attachment of the heteroatoms present on the stabilizing agent molecules that form a part of the hybrid lipid submonolayer, the components of the composite do not dissociate from the surface or exchange to render the membrane permeable to oxidants that react with the nanoparticle surface and/or surfactants that disrupt membrane integrity. In some embodiments, the hybrid lipid submonolayer is compatible with metal nanoparticles that can be customized in terms of their shape, size, and composition, which can be varied to tune their optical and electronic properties for use as contrast agents (e.g., in X-ray, CT, MRI, and OCT imaging techniques) and photothermal therapy. By way of example, FIG. 1 provides data showing that nanoparticle composite shape can be used to influence the UV-vis absorbance of the nanoparticle composite. For example, as shown by FIG. 1, differently shaped nanoparticle composites (e.g., composites 100, 102, and 104 shown in FIG. 2) behave differently in terms of wavelength absorbance and thus can be distinctly identified. The spherical nanoparticle composite 100 absorbs at a shorter wavelength than the rod-shaped composite 102, and the triangular-shaped nanoparticle composite 104 exhibits absorbance at an even longer wavelength. FIG. 3 provides a TEM image of representative nanoparticle composites.

In particular disclosed embodiments, the nanoparticle composites disclosed herein comprise a nanoparticle core and one or more covalently coupled stabilizing agent molecules. The nanoparticle core can comprise silver, gold, iron, gadolinium, any oxides thereof, and/or other metals. The nanoparticle core can have a shape that is selected according to the method in which the nanoparticle composite will be used. For example, as discussed above, the nanoparticle core can be spherical, ellipsoidal, rod-shaped, triangular, octagonal, or other shapes typically observed for nanoparticles. Exemplary shapes of nanoparticle composites are illustrated in FIGS. 2 and 3. In particular disclosed embodiments, the shape of the nanoparticle core can be controlled and/or maintained by incorporation of the hybrid lipid submonolayers to prevent shape distortion upon exposure to environments that might otherwise affect the shape of the nanoparticle. For example, the hybrid lipid bilayers comprising hybrid lipid submonolayers can prevent ion dissociation of ions generated from the nanoparticle core, which typically results in degradation of the nanoparticle core shape. By selecting and controlling the shape of the nanoparticle core, the optical and electronic properties of the composites can be tuned to produce nanomaterials that can be used with different imaging technologies. Modifying the shape of the nanoparticle composite can provide the ability to produce different UV-Vis spectra for each different shape (FIG. 1); thus, the nanoparticles can be visualized in vitro and/or in vivo without concurrent visual contamination from other biological molecules. For example, if one wants to avoid visualizing biological molecules that might absorb in the same wavelength region as a spherical nanoparticle composite (e.g., 420 nm to 475 nm, such as 430 nm and 470 nm, or 450 nm and 470 nm), then one can select a different shaped nanoparticle composite, such as a rod-like nanoparticle composite or triangular-shaped nanoparticle composite, that absorbs at a longer wavelength (e.g., 525 nm to 600 nm, such as 540 nm and 575 nm, or 550 nm and 560 nm for rod-like nanoparticle composites; or 620 nm and 700 nm, such as 630 nm and 660 nm, or 640 and 650 nm for triangular nanoparticle composites).

In some embodiments, the hybrid lipid bilayer membrane of the disclosed nanoparticle composites can be a hybrid bilayer comprising a lipid layer and a submonolayer comprising a stabilizing agent or an aggregation inhibitor. In yet additional embodiments, the hybrid lipid bilayer membrane of the disclosed nanoparticle composites can be a hybrid bilayer comprising a lipid layer and a hybrid submonolayer comprising a stabilizing agent in combination with aggregation inhibitors. The stabilizing agent molecule comprises an aliphatic tail and a heteroatom terminus that can covalently couple to the nanoparticle surface. In particular disclosed embodiments, the heteroatom is sulfur, oxygen, or nitrogen. In some embodiments, there are multiple such heteroatoms present on a single linker, such as the multiple oxygen atoms of a siloxane linker. One or more of these multiple heteroatoms can be covalently attached to the nanoparticle core. Such embodiments can be referred to herein as siloxane stabilizing agent molecules. In yet additional embodiments, the heteroatom is a nitrogen atom. The aliphatic chain of the stabilizing agent molecule typically comprises a hydrocarbon chain. In some embodiments, the hydrocarbon chain can comprise six or more carbon atoms in length. In particular disclosed embodiments, the aliphatic chain is 6 to 20 carbon atoms in length, such as 6 to 15 carbon atoms, or 6 to 10 carbon atoms. The aliphatic chain can comprise one or more sites of unsaturation, or it can be fully saturated. In particular disclosed embodiments, the aliphatic chain can further comprise a polar functional group on its terminus (that is, the terminus opposite that of the terminus comprising the covalently bound heteroatom). Suitable polar functional groups include, but are not limited to a carboxylic acid, an ester, or the like. In some embodiments, the stabilizing agent molecules comprise a heteroatom selected from sulfur or nitrogen. In embodiments using gold nanoparticles, the heteroatom typically is sulfur. In embodiments using silver nanoparticles, the heteroatom typically is nitrogen.

The hybrid lipid bilayer also can comprises an aggregation inhibitor molecule, which can be a molecule that associates with the nanoparticle core through hydrophobic interactions. For example, the aggregation inhibitors can form part of the hybrid lipid submonolayer (which can comprise a monolayer of aggregation inhibitor molecules and/or stabilizing agents). In yet additional embodiments, the aggregation inhibitors can be part of a lipid layer that forms part of the hybrid lipid bilayer membrane as some aggregation inhibitors can also constitute lipids. Aggregation inhibitors are molecules comprising a hydrophobic chain and a polar terminus that interacts with an aqueous environment, thereby forcing the hydrophobic chain to accumulate towards the nanoparticle surface. In some embodiments, the polar terminus comprises a functional group having a charged moiety (such as a positively charged or negatively charged moiety). In some embodiments, the polar terminus can comprise a carboxylate group, a substituted ammonium group (e.g., $-NH_2R^+$, $-NHR_2^+$, $-NR_3^+$, wherein each R independently is selected from aliphatic, heteroaliphatic, aryl, or heteroaryl), a phosphate group, or a combination thereof. In some embodiments, the hydrophobic chain can comprise two to 20 carbon atoms. In yet additional embodiments, the aggregation inhibitor molecule can be used to facilitate formation of the lipid membrane around the nanoparticle core, which will interact with the submonolayer to form the hybrid membrane (or hybrid lipid bilayer membrane), wherein a plurality of aggregation inhibitor molecules associate so as to form the lipid membrane. In such embodiments, the polar terminus of one aggregation inhibitor molecule interacts with the nanoparticle core and the hydrophobic chain interacts with the hydrophobic chain of another aggregation inhibitor molecule. In some embodiments, the polar terminus is not covalently attached to the surface of the nanoparticle core, but can interact with the core through non-covalent forces (e.g., electrostatic interactions, such as ionic interactions, hydrogen bonding, or combinations thereof; Van der Waals forces, and the hydrophobic effect). The hydrophobic chains of the plurality of aggregation inhibitors are thus positioned so as to avoid a surrounding aqueous environment. In some embodiments, the lipid membrane can be formed by one or more lipids that are different from the aggregation inhibitors. The stability of membrane-coated nanoparticles can be obtained using the hydrophobic stabilizing agent molecules disclosed herein that covalently attach to the nanoparticle core so as to anchor membranes to the surface of the nanoparticle core.

The nanoparticle composites disclosed herein can be combined with imaging components and/or targeting agents to facilitate tumor imaging, localization of the nanoparticles, and imaging of nanoparticle delivery. In some embodiments, imaging components (or signal generating moieties) can be used and can include pH-sensitive dyes (e.g., dyes that emit a detectable signal upon a change in its surrounding environment, or dyes where a detectable signal is quenched upon a change in its surrounding environment), such a chromogens, fluorophores, or other visualization moieties. Exemplary chromogens include, but are not limited to rhodamine, nitrophenyl-β-D-galactopyranoside (ONPG), 5-bromo-4-chloro-3-indolyl-β-galactopyranoside (X-Gal), methylumbelliferyl-β-D-galactopyranoside (MU-Gal), p-nitrophenyl-α-D-galactopyranoside (PNP), 5-bromo-4-chloro-3-indolyl-β-glucuronide (X-Gluc), 3-amino-9-ethylcarbazol (AEC), 10-acetyl-3,7-dihydroxyphenoxazine (ADHP), diaminobenzidine (DAB), tetramethylbenzidine (TMB), 2,2'-azino-di-[3-ethylbenzothiazoline sulphonate] (ABTS), o-dianisidine, 4-chloronaphthol (4-CN), and o-phenylenediamine (OPD).

Exemplary fluorophores include, but are not limited to 4-acetamido-4'-isothiocyanatostilbene-2,2'disulfonic acid, acridine and derivatives thereof, such as acridine and acridine isothiocyanate, 5-(2'-aminoethyl)aminonaphthalene-1-sulfonic acid (EDANS), 4-amino-N-[3-vinylsulfonyl)phenyl]naphthalimide-3,5 disulfonate (*Lucifer* Yellow VS), N-(4-anilino-1-naphthyl)maleimide, anthranilamide, Brilliant Yellow, coumarin and derivatives thereof, such as coumarin, 7-amino-4-methylcoumarin (AMC, Coumarin 120), 7-amino-4-trifluoromethylcoulaurin (Coumaran 151); cyanosine; 4',6-diaminidino-2-phenylindole (DAPI); 5', 5''-dibromopyrogallol-sulfonephthalein (Bromopyrogallol Red); 7-diethylamino-3-(4'-isothiocyanatophenyl)-4-methylcoumarin; diethylenetriamine pentaacetate; 4,4'-diisothiocyanatodihydro-stilbene-2,2'-disulfonic acid; 4,4'-diisothiocyanatostilbene-2,2'-disulfonic acid; 5-[dimethylamino] naphthalene-1-sulfonyl chloride (DNS, dansyl chloride); 4-dimethylaminophenylazophenyl-4'-isothiocyanate (DAB ITC); eosin and derivatives thereof, such as eosin and eosin isothiocyanate; erythrosin and derivatives thereof, such as erythrosin B and erythrosin isothiocyanate; ethidium; fluorescein and derivatives thereof, such as 5-carboxyfluorescein (FAM), 5-(4,6-dichlorotriazin-2-yl)aminofluorescein (DTAF), 2'7'-dimethoxy-4'5'-dichloro-6-carboxyfluorescein (JOE), fluorescein, fluorescein isothiocyanate (FITC), and QFITC (XRITC); fluorescamine; IR144; IR1446; Malachite Green isothiocyanate; 4-methylumbelliferone; ortho cresolphthalein; nitrotyrosine; pararosaniline; Phenol Red; B-phycoerythrin; o-phthaldialdehyde; pyrene and derivatives thereof, such as pyrene, pyrene butyrate and succinimidyl 1-pyrene butyrate; Reactive Red 4; rhodamine and derivatives thereof, such as 6-carboxy-X-rhodamine (ROX), 6-carboxyrhodamine (R6G), lissamine rhodamine B sulfonyl chloride, rhodamine (Rhod), rhodamine B, rhodamine 123, rhodamine X isothiocyanate, sulforhodamine B, sulforhodamine 101 and sulfonyl chloride derivative of sulforhodamine 101 (Texas Red); N,N,N',N'-tetramethyl-6-carboxyrhodamine (TAMRA); tetramethyl rhodamine; tetramethyl rhodamine isothiocyanate (TRITC); riboflavin; rosolic acid and terbium chelate derivatives; LightCycler Red 640; Cy5.5; and Cy5.

Figure 4:
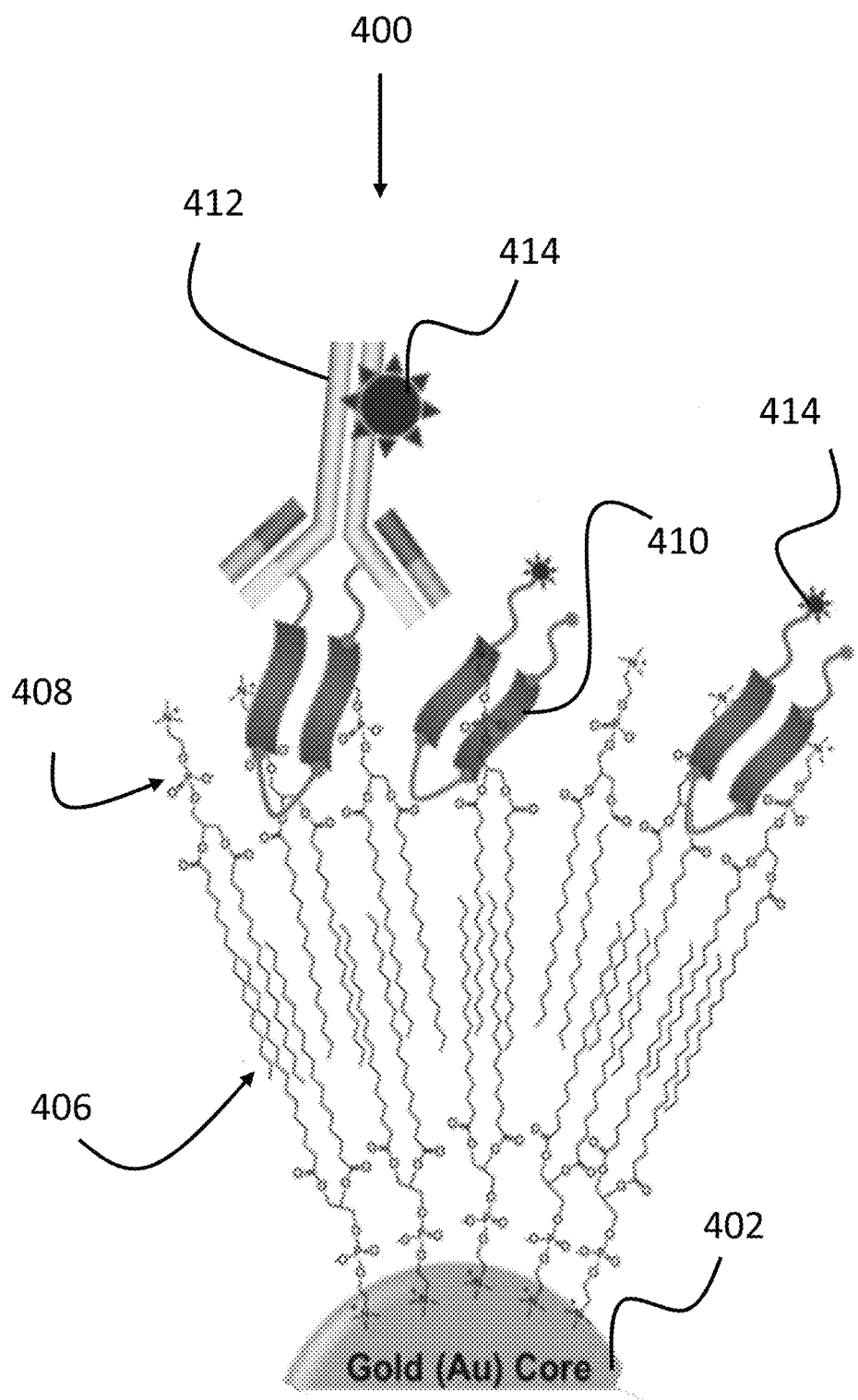
FIG. 4 is an illustration of a representative nanoparticle composite described herein, which further comprises associated protein molecules (410), antibodies (412), and signal generating moieties (e.g., fluorophores 414).
Figure 6:
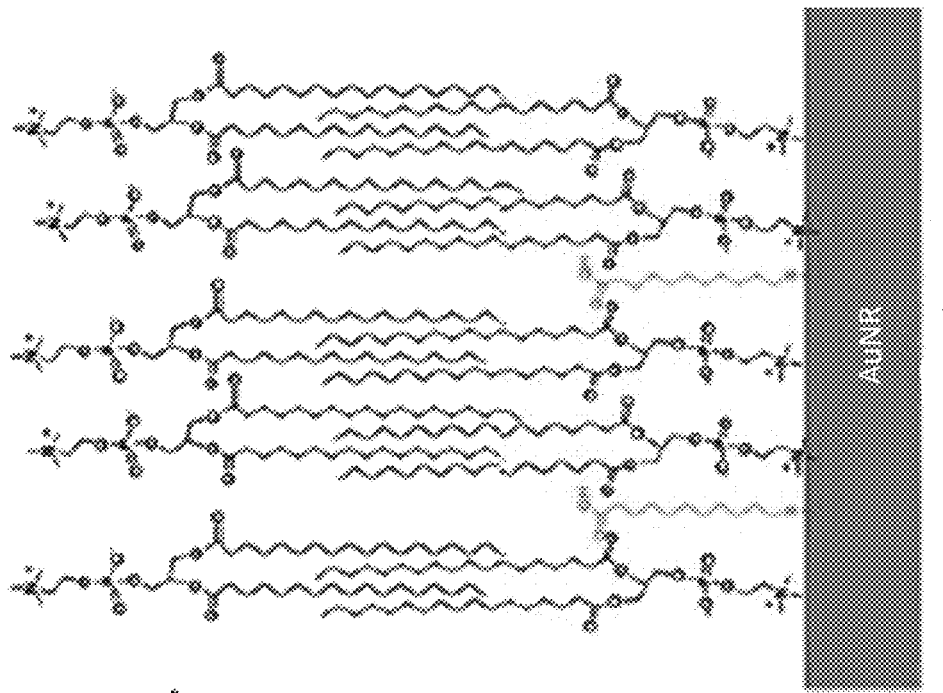
FIG. 6 is an illustration of a representative nanoparticle composite disclosed herein that can be used for X-ray and/or optical coherence tomography (OCT) imaging techniques.
Figure 5:
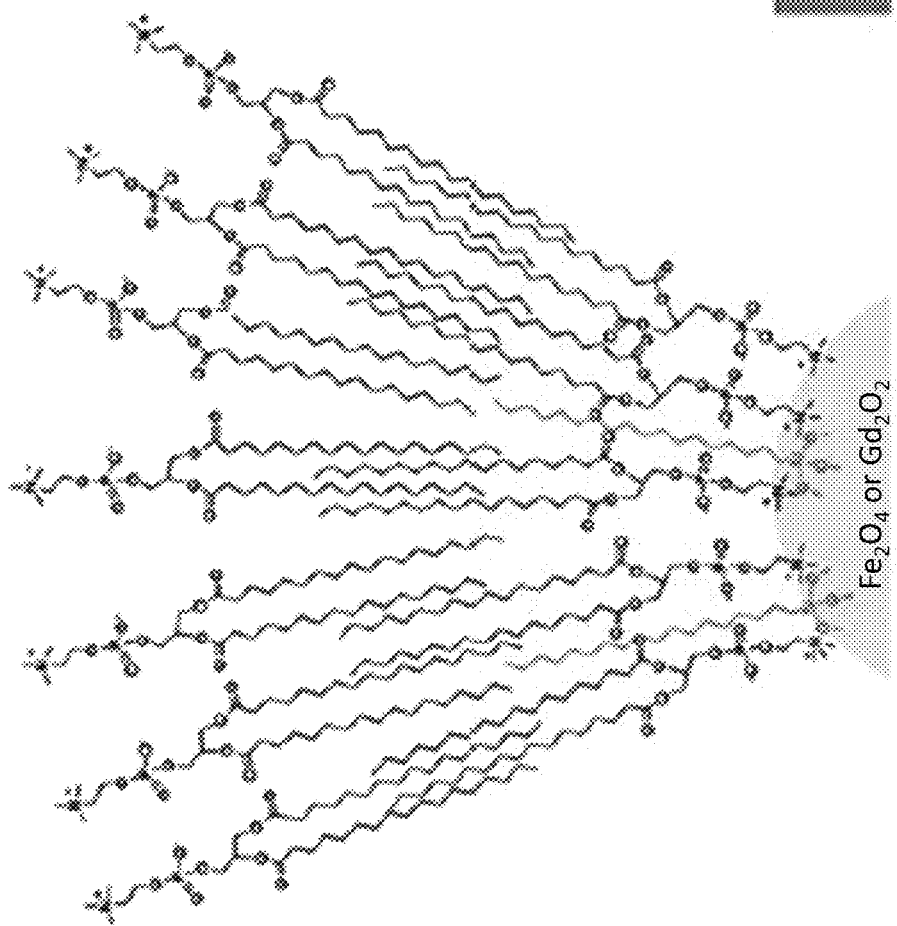
FIG. 5 is an illustration of a representative nanoparticle composite disclosed herein that can be used for MRI imaging.

Exemplary targeting agents include, but are not limited to Anti-HER-2 antibody, folic acid, sugar moieties, and peptides (e.g., Arg-Gly-Asp peptides). An exemplary composite comprising a targeting agent and imaging agent is illustrated in FIG. 4 (while the stabilizing agent molecules are not illustrated, they can be positioned between the illustrated lipid groups). With reference to FIG. 4, the illustrated nanoparticle composite 400 comprises a gold core 402 with a plurality of exposed phosphatidylcholine ligands 406 and 408, which form a membrane layer and allow for recognition and binding of protein 410, to which antibody 412 can bind. By implementing fluorophore labels 414, visualization of the nanoparticle composite is possible. Additional exemplary composites are illustrated in FIGS. 5-9.

IV. Methods of Making Nanoparticle Composites

Figure 10:
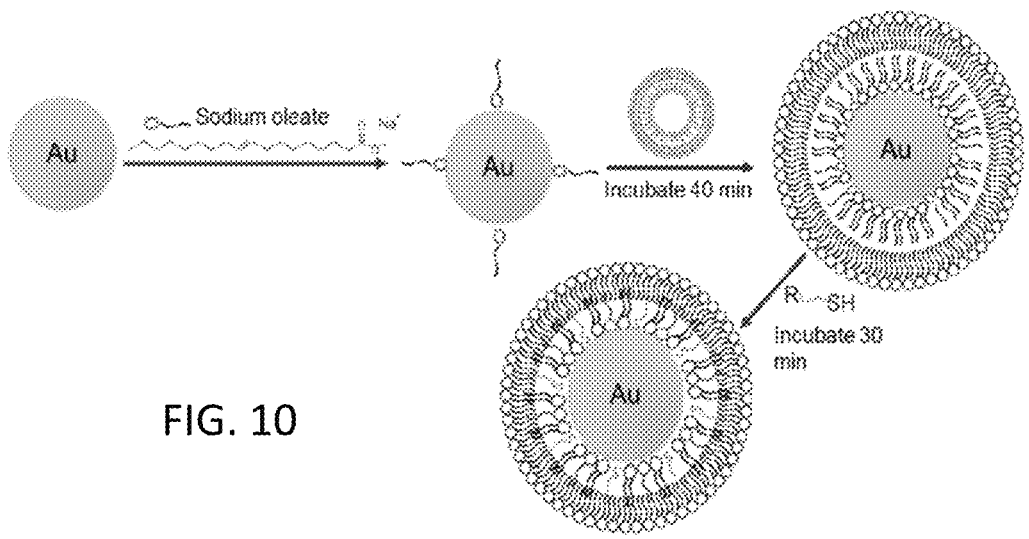
FIG. 10 is a schematic illustration of a representative method for making a lipid-coated nanoparticle composite described herein.
Figure 11:
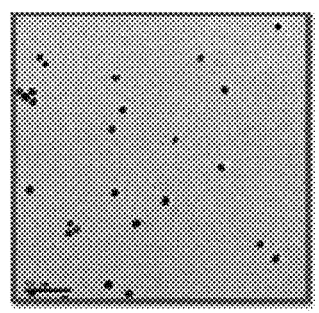
FIG. 11 is a TEM image of representative lipid-coated nanoparticles described herein.

The nanoparticle composites disclosed herein can be made by exposing a nanoparticle core to a first member of the hybrid lipid submonolayer, such as aggregation inhibitors. In some embodiments, the aggregation inhibitors can be prepared from sodium oleate. The method can further comprise exposing the nanoparticle core to a lipid membrane, such as a bilayer lipid membrane (e.g., a membrane comprising phosphatidylcholine), and further exposing the nanoparticle core to a second member of the hybrid lipid submonolayer, such as a stabilizing agent molecule comprising an aliphatic chain and a heteroatom terminus that can covalently bind to a surface of the nanoparticle core. In some embodiments, these method steps can be performed in any order, sequentially or simultaneously. An exemplary method is illustrated schematically in FIG. 10. While the embodiment illustrated in FIG. 10 illustrates a gold nanoparticle core and thiol ligands attached to the core as the stabilizing agent molecule, other types of nanoparticle cores are contemplated (e.g., silver, silver oxides, gadolinium oxides, iron, iron oxides and the like) as are other ligands that do not contain a thiol group (e.g., ligands comprising amine groups, siloxane groups, and the like). FIG. 11 provides a TEM image of exemplary hybrid lipid bilayer-coated gold nanoparticle composites made according to methods described herein. As can be seen in FIG. 11, the HBM-coated nanoparticle composites are homogeneously distributed.

In particular disclosed embodiments, the optical density and diameter of the nanoparticle (without any functionalization) and surface area of the lipids can be used to calculate the amount of lipids (and/or number of lipid molecules) needed to cover a nanoparticle of a given diameter. This technique facilitates minimization of the amount of excess lipids left over in the sample after assembly of the lipid-coated nanoparticles; such excess lipid molecules can be difficult to remove fully from preparations and may, for instance, complicate toxicity studies. Such methods constitute an improvement over conventional techniques as purification steps can be avoided and/or simplified and complicated or tainted results can be avoided. In some embodiments, the nanoparticles can also be purified using ultracentrifugation to remove free molecules, including free lipids or other molecules integrated into or associated with the nanoparticles. In particular disclosed embodiments, the purity of the nanoparticle composites can be controlled by reducing the number of free lipids that are used to make the nanoparticles or that can be dissociated from the nanoparticle during its synthesis by evaluating the number of stabilizing agent molecules and/or aggregation inhibitors that populate the nanoparticle surface based on the optical density and diameter of the nanoparticle and reducing the number of lipid molecules based on that number to reduce or avoid excess lipid or other molecules from the end product. Additional exemplary methods for controlling the amount of excess lipids are described in the Examples section of the present disclosure.

Figure 7:
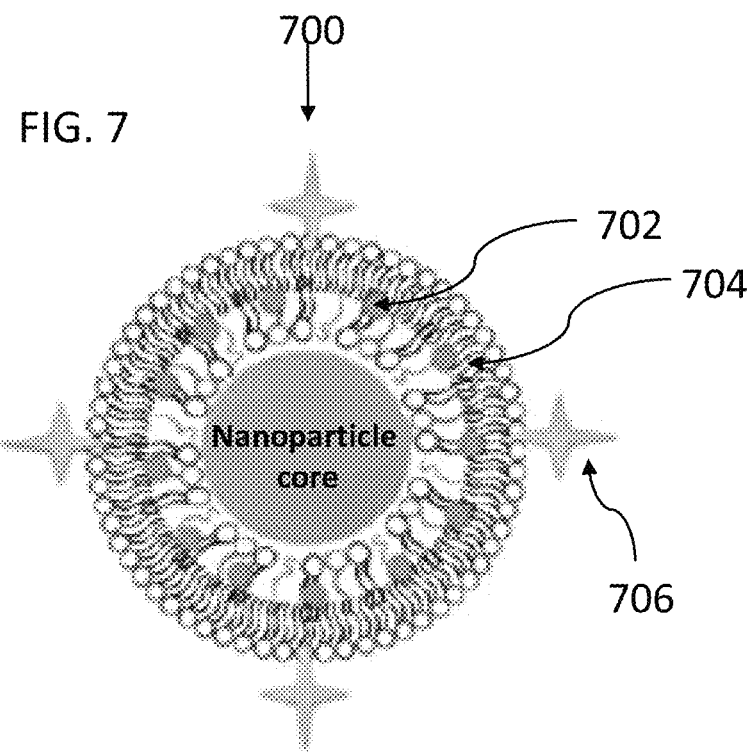
FIG. 7 is an illustration of a representative nanoparticle composite (700) comprising drug components (702) encapsulated in a hydrophobic bilayer (704) and targeting moieties (706) conjugated to lipids of the bilayer.
Figure 8:
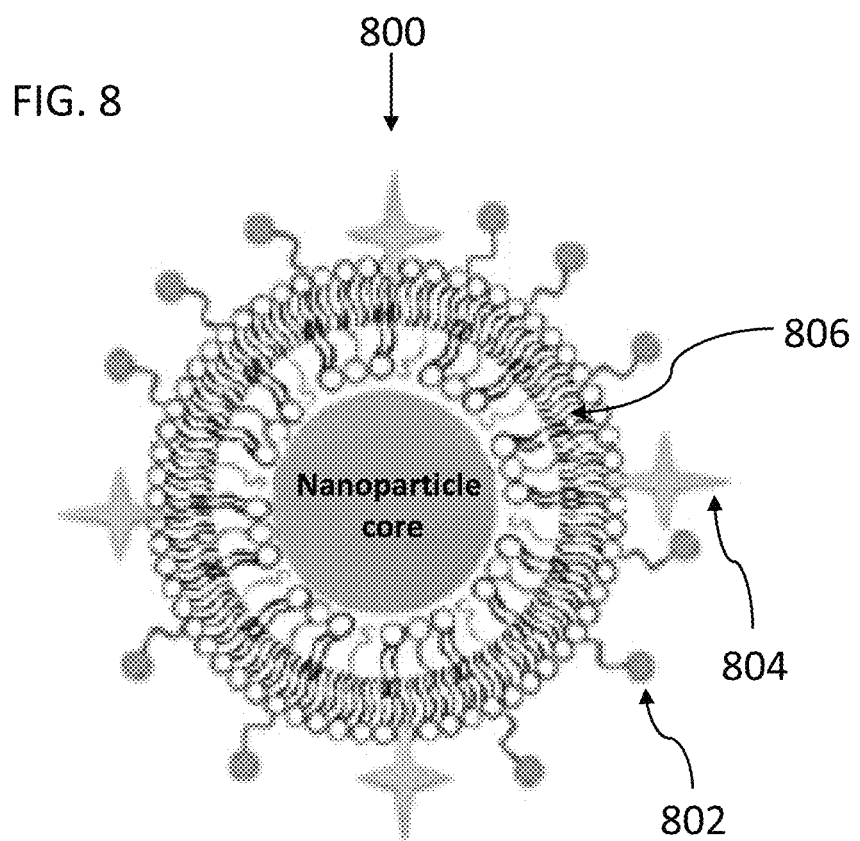
FIG. 8 is an illustration of a representative nanoparticle composite (800) comprising drug components (802) and targeting moieties (804), both of which are conjugated to lipids of the bilayer (806).
Figure 9:
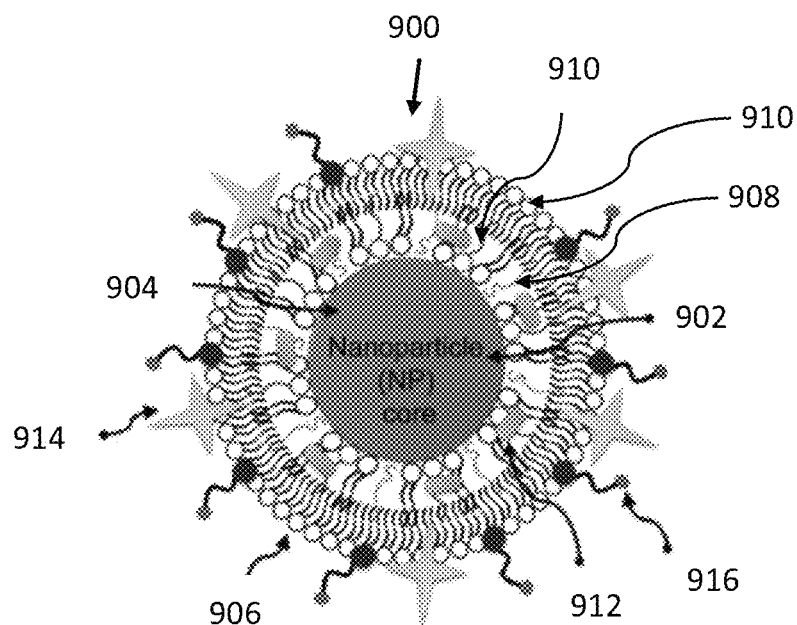
FIG. 9 is an illustration of a representative nanoparticle composite disclosed herein.

In particular disclosed embodiments, the nanoparticle composites disclosed herein can be coupled to or can incorporate therapeutic compounds such as drugs or toxic molecules, and/or targeting or recognition molecules, such as cell or cancer recognition molecules. In some embodiments, anti-cancer drugs, such as doxorubicin and Paclitaxel, can be incorporated into the lipid membranes of the nanoparticles by preparing liposomes with hydrophobic drugs as thin films and then re-suspending them into 10 mM PBS pH 8 buffer to form liposomes before encapsulation onto the nanoparticles. In some embodiments, the drugs are associated to the nanoparticle composite with a thioester linkage capable of being cleaved with a reactive oxygen species and/or an esterase enzyme. For example, FIG. 7 provides an illustration of a nanoparticle composite 700, which comprises drug components 702 embedded within the hydrophobic bilayer 704 of the nanoparticle composite and targeting moieties 706 conjugated to lipids of the membrane. In some embodiments, drugs can be directly conjugate to lipids through EDC/NHS coupling chemistry. For example, as illustrated in FIG. 8, targeting moieties 804 can be conjugated to lipids of the membrane 806 as can drug components 802. The coupled drug-lipid molecules are then stoichiometrically mixed with other lipids, such as PC lipids in various ratios to form lipid membranes. Another exemplary nanoparticle composite is illustrated in FIG. 9, which illustrates an embodiment 900 where a nanoparticle core 902 can comprise a photothermal agent 904 and is surrounded by hybrid lipid bilayer membrane 906, which comprises stabilizing agents 908 and aggregation inhibitors 910 (which can be the same or different types of molecules). Membrane 906 can surround drug components 912 that are positioned between the membrane and the nanoparticle core 902. Within the membrane, target moieties 914 and conjugated fluorophores 916 can be included.

In yet additional embodiments, the nanoparticles disclosed herein can be used to target cancer cells by coupling the lipids of the nanoparticles to folic acid or HER-2 recognition groups overexpressed on cancer cells. In some embodiments, 1,2-distearoyl-sn-glycero-3-phosphoethanolamine-N-[folate(polyethylene glycol)-5000 (folic acid-PEG-DSPE) or 1,2-dipalmitoyl-sn-glycero-3-phosphoethanolamine-N-(6-((folate)amino)hexanoyl) (sodium salt) can be used. In yet additional embodiments, the trastuzumab antibody, which targets HER-2 epidermal growth factor on breast cancers, can be coupled to liposomes used with the nanoparticles disclosed herein through EDC/NHS coupling chemistry.

V. Methods of Using Nanoparticle Composites

Figure 12:
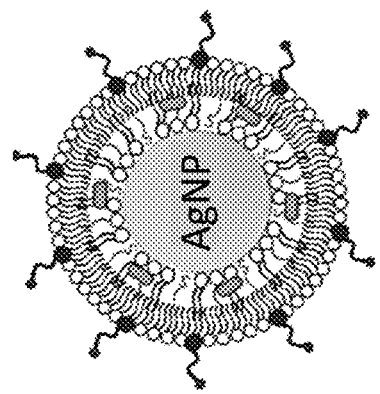
FIG. 12 is an illustration of a nanoparticle composite 1200 wherein the membrane composition can be tuned for site-directed delivery of drug 1210; different membrane components 1202, 1204, 1206, and 1208 can be selected to become part of the membrane of nanoparticle composite 1200 and can be used to direct delivery and/or visual detection of drug components 1210, which can be the same or different.
Figure 12:
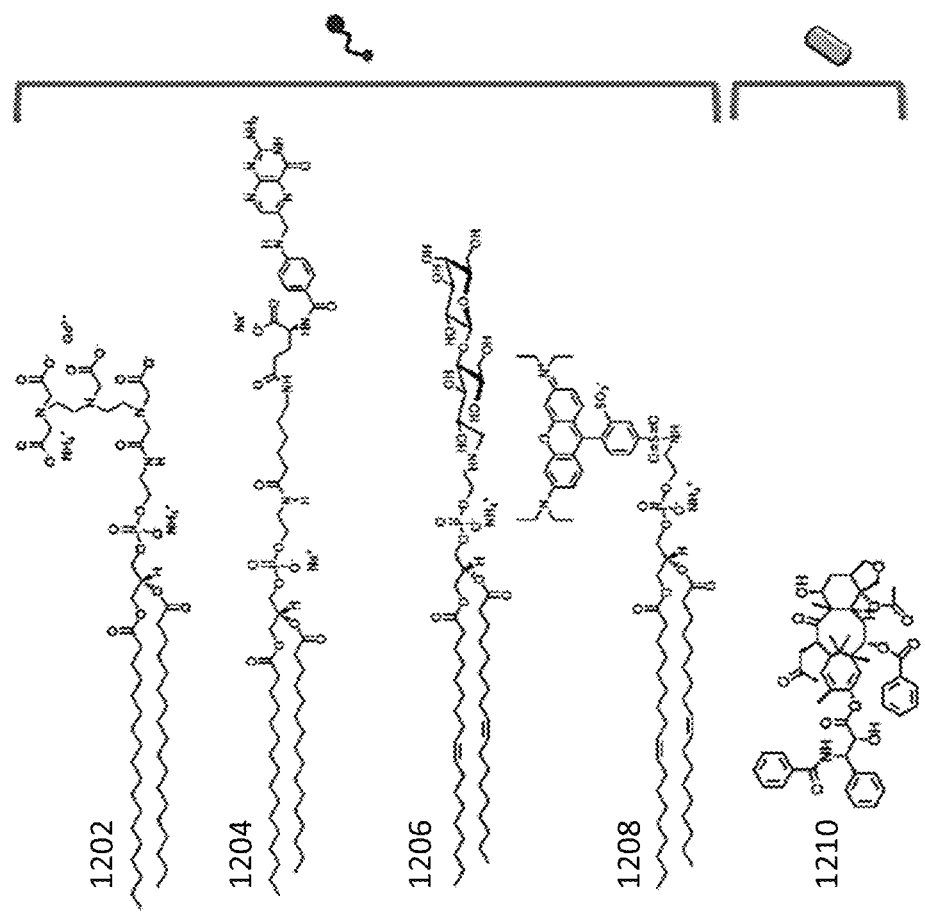

Disclosed herein are embodiments of methods of using the disclosed nanoparticle composites. In particular disclosed embodiments, the nanoparticle composites can be used for drug delivery, imaging, and disease treatment. In some embodiments, the nanoparticle composites can be used to deliver anti-cancer drugs. Exemplary nanoparticle composites that can be used for drug delivery are illustrated in FIG. 12. As illustrated by FIG. 12, various different membrane components (1202-1208) can be used in the hybrid membrane. In yet additional embodiments, the nanoparticle composites can be used in imaging technologies, such as X-ray-based CT, OCT, and MRI. For example, the nanoparticle composites can be used as CT imaging enhancers in vivo, MRI contrast agents, and OCT contrast agents. In particular disclosed embodiments, the nanoparticle composites can comprise gold nanoparticle cores or silver nanoparticle cores with a hybrid lipid submonolayer that can be further modified to include one or more different types of associated molecules or associated lipid membranes (such as shown by FIG. 12). The use of the hybrid lipid submonolayer, which comprises one or more covalently-bound stabilizing agent molecules, allows for incorporation and close association of other types of molecules and/or lipid membranes.

In yet other embodiments, such as those where the nanoparticle composites are used as MRI contrast agents, the nanoparticle composites can comprise iron oxide or gadolinium oxide and a hybrid lipid submonolayer comprising one or more stabilizing agent molecules that covalently bind to the iron oxide or gadolinium oxide core. In such embodiments, the stabilizing agent molecule comprises one or more oxygen atoms, such as one or more oxygen atoms of a siloxane group. In some embodiments, the hybrid lipid submonolayer further includes aggregation inhibitors and further can be combined with a lipid layer to form a hybrid lipid bilayer membrane.

For embodiments where the nanoparticle composites are used as OCT contrast agents, the nanoparticle composite can comprise gold nanorods and hybrid lipid submonolayers comprising covalently bound stabilizing agent molecules and/or aggregation inhibitors, such as those disclosed herein. In some embodiments, the stabilizing agent molecules can comprise a thiol group coupled to an aliphatic chain and can further include a polar moiety, such as a carboxylic acid. The thiol group covalently attaches to the gold nanorod and the carboxylic acid moiety facilitates suspension of the nanoparticle composite in an aqueous environment. Such nanoparticle composite embodiments can further comprise lipid membranes associated with the stabilizing agent molecules, such as tetramethylammonium/phosphate-containing lipids (e.g., L-α-phosphatidylcholine).

In some embodiments, the methods can comprise selecting a nanoparticle composite wherein the nanoparticle core has a particular shape. By selecting a particular shape of the nanoparticle composite, the wavelength at which the nanoparticle composite will absorb energy can be controlled or influenced. Such composites can be administered to a subject and their presence detected using an energy source that produces energy at the wavelength at which the nanoparticle composite will absorb. In some embodiments, such methods can be performed in vitro by contacting a sample obtained from a subject.

VI. Examples

Example 1

Figure 13:
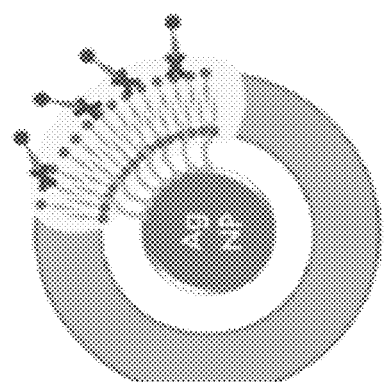
FIG. 13 shows results obtained from analyzing the detergent-resistance of a representative nanoparticle composite, comprising a hybrid membrane including phosphatidylcholine ("PC") and hexanethiol ("HT") groups.
Figure 13:
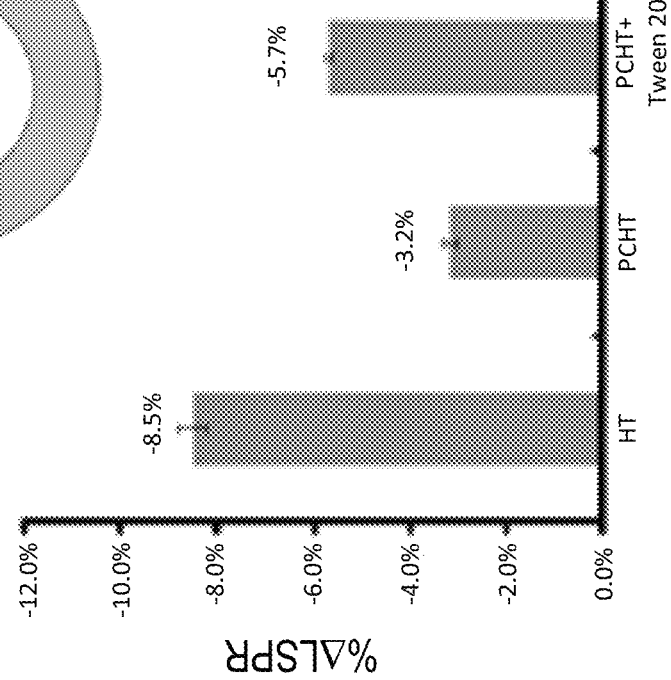
Figure 14:
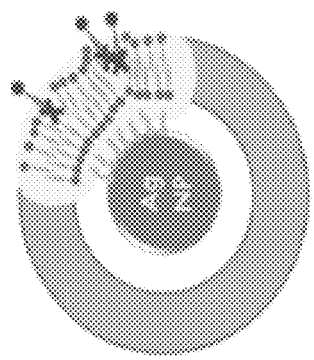
FIG. 14 shows results obtained from analyzing the detergent-resistance of a representative nanoparticle composite, comprising a hybrid membrane including phosphatidylcholine ("PC") and propanethiol ("PT") groups.
Figure 14:
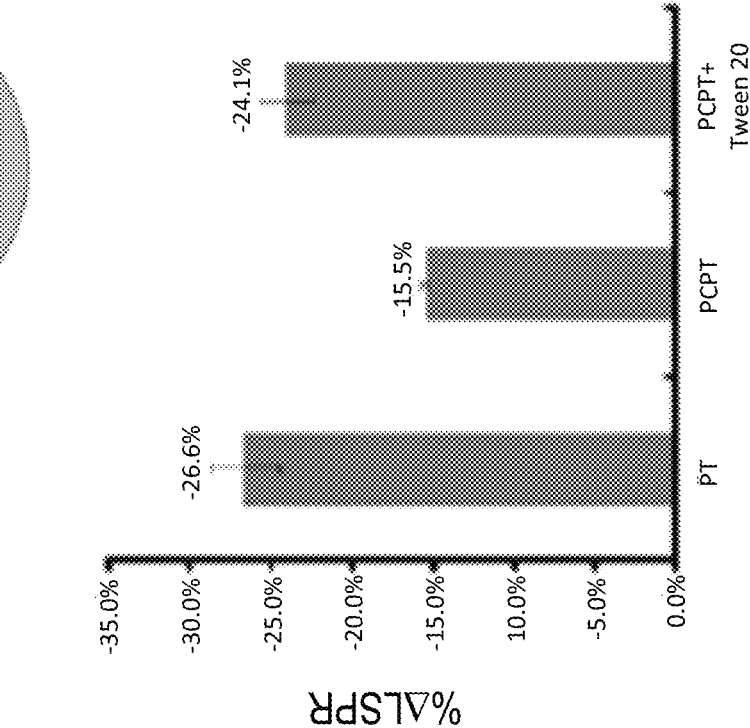
Figure 15:
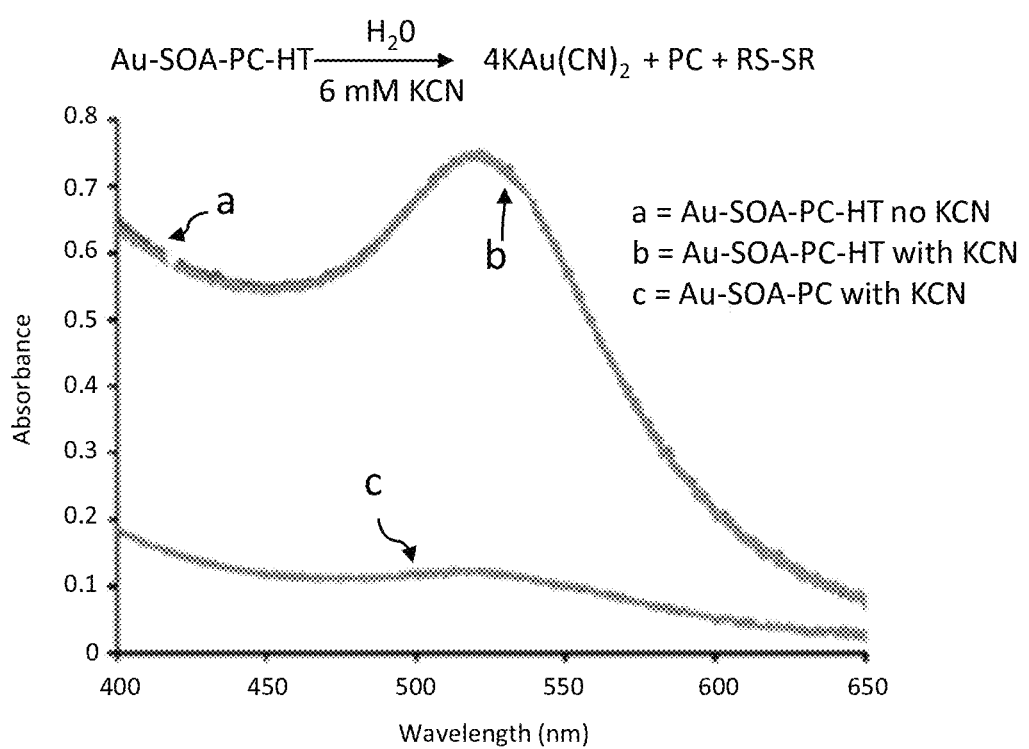
FIG. 15 is a graph of absorbance as a function of wavelength (nm) illustrating results from cyanide etching studies of representative nanoparticle composite embodiments; these results confirm that HBM-coated nanoparticle composites described herein can resist etching of the nanoparticle core.

UV-Vis, DLS, and TEM can be used to evaluate the size and morphology distributions of the nanoparticle composites disclosed herein. A KCN etch test can be used to examine the stability of the HBM-coated AuNP and AgNPs, while oxalic acid is used to etch HBM-coated $Fe_3O_4$ and $Gd_2O_3$ nanoparticles. DLS and TEM are used to determine if there is a change in the nanoparticle size distribution in the presence of the etchants. These studies will confirm that there is no reorganization of the anchored lipid membrane that would lead to instability and penetration of the etchants. The shelf-life of nanoparticle batches are tested immediately, 1 week, 1 month and 3 months after preparation. Positive and negative staining agents such as uranyl acetate are used to investigate the lipid coverage on the nanoparticle surface as membrane composition is varied. To quantify drug loading and cancer recognition groups, the nanoparticles are etched, purified by centrifugation, and analyzed using $^1$H NMR and UV-Vis analysis. Exemplary results from etching test embodiments are illustrated in FIGS. 13-15.

Example 2

To determine if the HBM-coated nanoparticles recognize folate receptors or HER-2 on cells cellular uptake studies are performed using commercially available HeLa, L929, and A549 cells according to a similar literature protocol. Cancer cell lines, ovarian (SK-OV-3), breast (ZR-75-1), and lung (A 549), are purchased from Reaction Biology Corp. Cells are imaged after incubation with 1×101 to 1×1015 nanoparticles/mL and washing steps using a confocal microscope. Additionally, cells are thin-sectioned, placed on copper grids, and stained with lead (II) citrate for visual detection by TEM. The LSPR band of the AuNPs is used to determine concentration of AuNPs during uptake into the HeLa cells. L929 mouse fibroblast cells with no folate receptors are expected to have minimal to no uptake of AuNPs compared to A549 cells rich with folate receptors. Higher HBM-coated nanoparticles nanoparticle uptake in (SK-OV-3) breast (ZR-75-1), and lung (A549) will occur where there is a higher concentration of folate and HER-2 receptors.

Example 3

To examine if the HBM-coated nanoparticles induce toxicity to cancerous and healthy cell lines, the nanoparticles are incubated with the cell lines and a commercially available cell-viability assay is used to determine cell death. Cells are incubated under serum free conditions using DMEM containing 1% (v/v) glutamine, 1% (v/v) penicillin/streptomycin, 0.5% amphotericin B and 2.6 g dL$^{-1}$ of bovine serum albumin (BSA: Sigma Aldrich, AU) in a humidified atmosphere at 37° C. for one day. At least three repeats of three independent measurements (n=3) are performed for each condition. Results are expressed as mean and standard error of the mean. The variance of each group of data is compared with a two-tailed F—test following an F—distribution under the null hypothesis (data sets have equal variances). A two-tailed t-test following a Student's t distribution under null hypothesis (data sets have equal means) is used to compare the means of different groups of data. During the data analysis, a probability lower than 0.05 ($p<0.05$) will be considered to be statistically significant.

The embryonic zebrafish model has emerged as a useful and valuable model of vertebrate biology and concomitantly, human toxicology. This model system offers the power of whole-animal investigations (e.g., intact organism, functional homeostatic feedback mechanisms and intercellular signaling) with the convenience of cell culture (e.g., cost- and time-efficient, minimal infrastructure, small quantities of nanomaterial solutions required). A dynamic in vivo whole animal assay can be used to reveal whether a nanomaterial is potentially toxic at multiple levels of biological organization (e.g., molecular, cellular, systems, organismal). Early developmental life stages are uniquely sensitive to environmental insult, due in part to the enormous changes in cellular differentiation, proliferation and migration to form the required cell types, tissues and organs. Thus, early developmental life stages are most ideal to determine if chemicals or nanomaterials are toxic. This model is advantageous because it allows full mechanistic interrogation of a nanomaterial's biological interactions, instead of purely descriptive data and is extensively used for investigating animal responses upon exposure to nanomaterials. Cell-to-cell communications and molecular signaling pathways affected in early embryonic development by nanomaterials serve as evidence of toxicity. Furthermore, the embryos are transparent so simple microscopic techniques are used to evaluate toxicity. Although the HBM-coated nanoparticles have built-in features that support biocompatibility, the nanomaterial-biological interactions will be evaluated to protect health and ensure safety. The bioinspired HBM-coated nanomaterials should have minimal toxicity and perturbation of cell-to-cell communications and molecular signaling pathways.

Fluorescence, dark field hyperspectral imaging techniques (HSI) and confocal microscopy will be used to examine physical features that correlate with toxicity and tissue biodistribution. In addition, nanoparticle plasmon resonance coupling (NPRC) effect observed with gold nanoparticles is an attractive attribute that serves as an analog to FRET. As a result this presents a unique opportunity to use these as an alternative imaging technologies to investigate uptake of nanoparticles in live cells and their subcellular localization using a dark field hyperspectral imaging technique. Biodistribution studies are expected to provide valuable information regarding nanoparticle localization in the tissues of the zebrafish. Digital images of anaesthetized zebrafish will be taken using a fluorescent microscope or HSI to visualize nanoparticle concentrations. This will help determine if the nanoparticles are limited to epithelial layers, brain tissue, eye, and heart.

In some embodiments, digital images of anaesthetized zebrafish will be taken using a fluorescent microscope or HSI to visualize nanoparticle concentrations. Uptake of the nanoparticles will be quantified and biodistribution will be determined using hyperspectral imaging analysis and confocal microscopy. Spectral libraries of the nanoparticles are acquired with a spectral imaging camera attached to a microscope. In vivo localization is determined by the location of the spectral signatures when compared to a spectral library. More targeted confocal microscopy will be used to elucidate cellular localization in vivo. In addition, nanoparticle plasmon resonance coupling (NPRC) effect observed with AuNPs is an attractive attribute that serves as an analog to FRET. Consequently, this presents a unique opportunity to use these as alternative imaging agents to investigate nanoparticle uptake in live cells and their subcellular localization using a dark field hyperspectral imaging technique.

Figure 16:
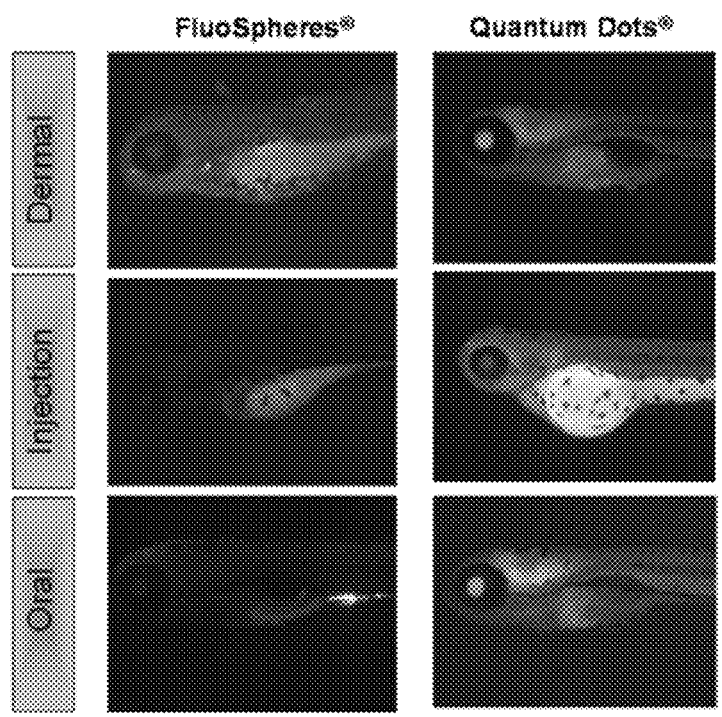
FIG. 16 shows the biodistribution of FluoSpheres® and QDots® administered via waterborne (dermal and oral) or microinjection (injection) exposure in zebrafish.

In vivo distributions were determined for embryonic zebrafish exposed (waterborne, injection, oral) to fluorescent FluoSphere® and Qdots® in order to evaluate the influence of exposure route and surface functionalization on uptake and biodistribution. A timeline for uptake from waterborne exposures is determined for FluoSphere® with carboxylated surface functionalization. Waterborne FluoSpheres® were observed in external epithelial tissues for the first 24 h, in the vasculature by 72 h and in the digestive tract by 144 hours. Distribution after uptake appeared to be greater for Qdots® than for FluoSpheres®, independent of the route of exposure (FIG. 16). Uptake from a dermal route was primarily limited to the epithelial layers and the yolk sac for carboxylated FluoSpheres®, but distribution to the brain region was achieved from waterborne exposure to Qdots®. Microinjection route also shows differential uptake and distribution. FluoSpheres® administered via the oral route of exposure were retained within the gastrointestinal tract; whereas, Qdots® were readily taken up across the gastrointestinal tract and distributed to the brain. A comparison of 20 nm carboxylate-modified Qdots® and FluoSpheres® revealed a strong influence of chemical composition on distribution independent of the surface functional groups. Additional evaluations of these nanomaterials can utilize confocal microscopy to localize the nanomaterials within cellular space. These studies demonstrate that the disclosed nanoparticle composites can be evaluated in a whole animal at minimal cost. Furthermore, nanomaterials can be easily visualized with transparent zebrafish model.

In some embodiments, embryonic zebrafish will be exposed in a 96-well plate format to 5-fold serial dilutions of nanoparticles from 16 parts per billion (ppb) to 250 parts per million (ppm). Exposures will begin at 8 hfp to ensure coverage of gastrulation and organogenesis, the periods of development most well conserved among vertebrates. Embryos will be evaluated at 24 hpf for viability, developmental progression and spontaneous movements. At 120 hpf, larval morphology (body axis, eye, snout, jaw, otic vesicle, notochord, heart, brain, somite, fin, morphometrics) will be assessed and behavioral endpoints will be thoroughly evaluated in vivo. The criteria for assessing nanomaterials-biological interactions or toxicity will be incidence of mortality, malformations, behavioral abnormalities and delayed development. Since zebrafish embryos are transparent, simple microscopic evaluations will be used to non-invasively observe development and assess for morphological or behavioral alterations throughout the exposure period. Waterborne-exposed embryos will be is described in Preliminary Studies, Harper. Control and nanomaterial-exposed groups will be statistically compared using one-way ANOVA (Sigma Stat, SPSS Inc., Chicago, Ill.). Kruskal-Wallis Analysis of Variance on Ranks will be used if the data violate normality or equal variance assumptions. The lethal concentration to cause 50% embryonic mortality (LC50) and the effective concentration to elicit sub-lethal responses in 50% of the organisms (EC50) will be calculated using probit and sigmoidal regression analyses, and the LOAEL will be calculated using an ANOVA (SPSS Inc., Chicago, Ill.).

Example 4

Hybrid PC-coated AuNPs were prepared by incubating bare gold colloids with sodium oleate (SOA), 30 nm liposomes prepared by sonication, and 10 nmole of hexanethiol (HT). Briefly, sodium oleate (2.2 µL of a 9.3 mM solution) was added to 10 nm gold nanoparticles (1 mL, 0.8 optical density (OD) at λmax=519 nm in $H_2O$) and stirred for 20 minutes. A dry, thin film was formed from a solution of PC (1.1 mg, 1.45 in 125 µL of CHCl3) in a glass scintillation vial by solvent evaporation under $N_2$. The film was additionally dried under vacuum for at least 12 h prior to re-suspension in 3 mL of 10 mM HEPES at pH 6.5 with 0.1% NaN3 followed by 90 minutes of sonication. From this stock, 45 µL (22.4 nmol of PC) was added to the nanoparticle solution and incubated for 40 minutes. This mixture was then incubated with 9 nmol of hexanethiol (0.9 µL of a 10 mM solution in ethanol) for 30 minutes. The solution was adjusted to a final buffer concentration of 10 mM HEPES at pH 6.5 with 0.1% $NaN_3$. Using Au-SOA-PC-HT a solution-based assay was developed for the detection of C-Reactive Protein, a prominent marker of inflammation. This work demonstrated that Au-SOA-OA-HT can mimic membranes, giving precedent that these nanomaterials could be used for Aβ detection.

Figure 17:
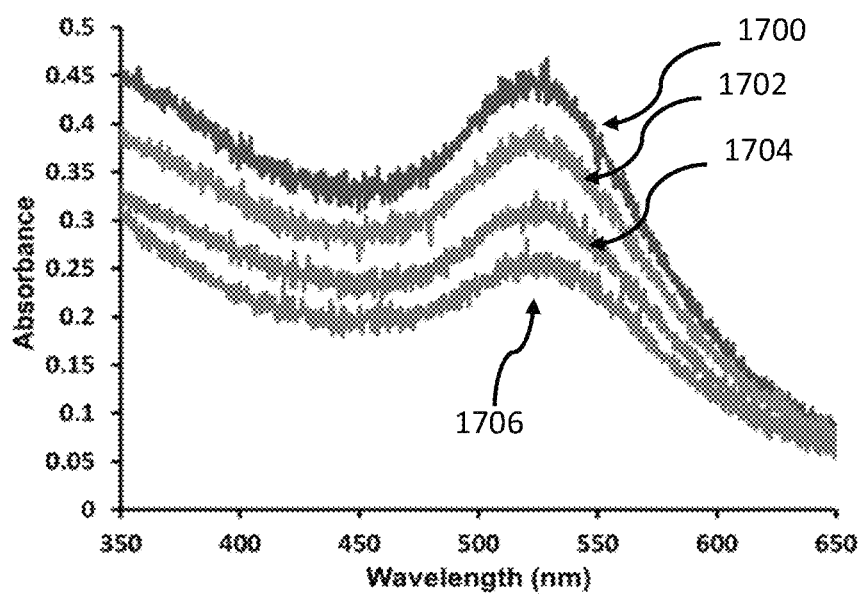
FIG. 17 is a graph of absorbance as a function of wavelength (nm), illustrating results obtained from analysis of TAMRA-A$\beta_{1-42}$ with Au-SOA-PC-HT (1700) after addition of 2 µL of 19 nM TAMRA-A$\beta_{1-42}$ (1702), or after addition of 2 µL 65 µM of $Cu^{II}$ (1704), or after addition of 3 mM cyanide (1706).

UV-vis and fluorescence studies were conducted to determine if Aβ has affinity towards Au-SOA-PC-HT. A decrease in the optical density of the LSPR band of Au-SOA-PC-HT was observed upon addition of fluorophore-labeled Aβ (TAMRA-Aβ$_{1-42}$) and $Cu^{II}$ ions (FIG. 17). This suggests TAMRA-Aβ$_{1-42}$ interacts with the membrane of the Au-SOA-PC-HT and this interaction is amplified by the presence of metal ions. To determine if changes in membrane integrity occurred, a cyanide (KCN) etch test was performed. KCN is known to oxidize $Au^0$ to $Au^I$ and serves as a probe for bare patches of gold surface. Upon addition of $CN^-$ a 16% decrease in optical density was observed after 30 minutes. This suggests that membrane integrity is compromised allowing $CN^-$ ions to penetrate hybrid bilayer to etch the $Au^0$ that was previously $CN^-$ resistant. Results from another example of using cyanide etching to evaluate anchoring of the membrane component of the HBM-coated nanoparticle composites are illustrated in FIG. 15. FIG. 15 shows a combined UV-Vis spectrum with different UV-Vis spectra of different nanoparticle composite embodiments after exposure to KCN, wherein spectrum "a" corresponds to an Au-SOA-PC-HT composite without KCN exposure, spectrum "b" corresponds to an Au-SOA-PC-HT composite after exposure to KCN, and spectrum "c" corresponds to an Au-SOA-PC composite after exposure to KCN. As can be seen by FIG. 15, the additional anchoring ligands (e.g., the thiol ligands illustrated in FIG. 10, or any other suitable anchoring ligands) can help anchor the membrane component to the nanoparticle core and thus prevent permeation of cyanide ions through the membrane.

Figure 18:
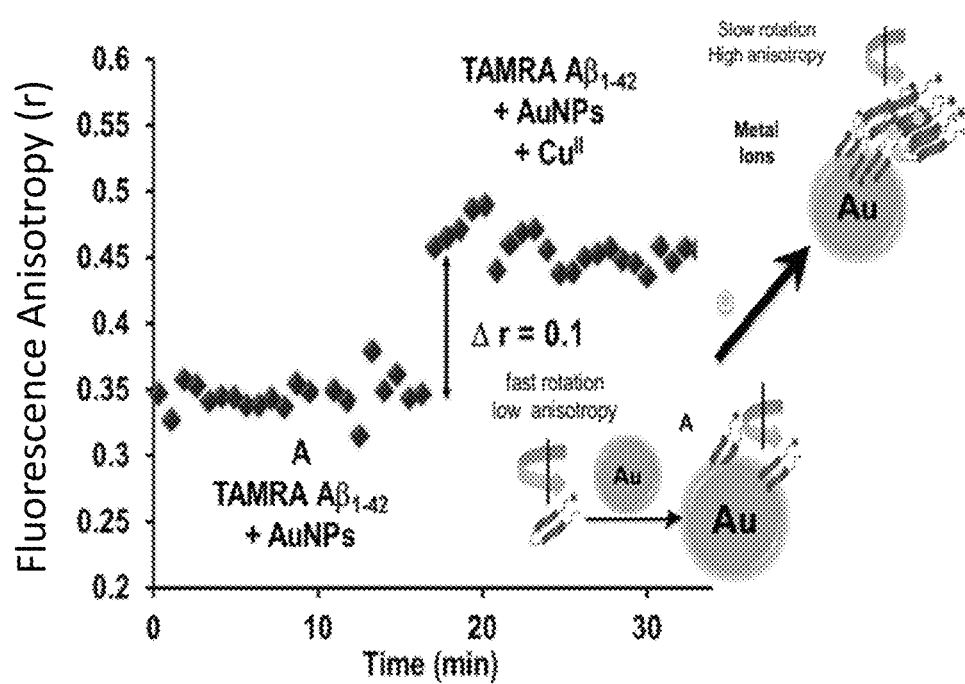
FIG. 18 is a graph of fluorescence anisotropy (r) as a function of wavelength (nm), illustrating results obtained from analysis of TAMRA-A$\beta_{1-42}$ with Au-SOA-PC-HT after 65 µM of $Cu^{II}$.

Fluorescence anisotropy also confirmed Aβ binding to AuNP surface. This technique reports on the change in the molecular rotation of the dye attached to the free TAMRA-Aβ$_{1-42}$ peptide and when it binds to something larger than itself under polarized light. The steady-state anisotropy (r) is derived from the following equation in which $r=(I_{VV}-GI_{VH})/(I_{VV}+2GI_{VH})$, where $I_{VV}$ and $I_{VH}$ are the fluorescence intensities, the subscripts indicate the orientation of the excitation and emission polarizer's, and $G=I_{HV}/I_{HH}$ is the wavelength dependent sensitivity of the instrument. In a typical experiment the intrinsic anisotropy of TAMRA-Aβ$_{1-42}$ ($r_{avg}$=0.12) increases in the presence of Au-SOA-PC-HT ($r_{avg}$=0.35) (FIG. 18). The resulting change in anisotropy (Δr=0.23) is due to a large change in the hydrodynamic radius (size) of the small TAMRA-Aβ$_{1-42}$ when it binds to the much larger Au-SOA-PC-HT nanoparticles. The addition of $Cu^{II}$ leads to an additional increase in anisotropy of TAMRA-Aβ$_{1-42}$ (Δr=0.11) indicating that rotation of the dye is further decreased (FIG. 18). Note that $Cu^{II}$ pre-incubated with TAMRA-Aβ$_{1-42}$ when added to Au-SOA-PC-HT has the same 0.11 change in anisotropy (FIG. 18). Possible explanations for the additional increase in r include metal ion reassembly of peptides bound to the membrane or bridging interactions between the Au-SOA-PC-HT-TAMRA-Aβ$_{1-42}$ species. Alternatively, metals could arrange TAMRA-Aβ$_{1-42}$ within the membrane bilayer to slow its molecular rotation. The change in r was also metal dependent where r was greatest for $Cu^{II}$>$Fe_{III}$>$Zn^{II}$ indicating that they have very different effects on the peptide. This technique can be useful to compare how metal type influences the formation of specific metallated-Aβ conformers that induce membrane disruption and lipid peroxidation.

Example 5

In this example, silver nanoparticle (AgNPs) composites were formed. $AgNO_3$ (43 mL of a 0.109 mM solution in $H_2O$) was combined with $H_2O_2$ (120 µL of 30% w/w) and $Na_3C_6H_3O_7$ (3.68 mL of a 34.2 mM in $H_2O$) in a 250 mL Erlenmeyer flask covered with aluminum foil to protect the solution from light exposure. The mixture was allowed to stir at 600 rpm with a medium sized stir bar for approximately 1 minute before a freshly prepared aqueous solution of $NaBH_4$ (360 µL of 100 mM in $H_2O$) was rapidly added to the center of the reaction vortex in the flask. $NaBH_4$ addition the solution resulted in a rapid color change from pale yellow to orange, followed by purple, and then finally stabilizing to blue over the course of approximately 2-3 minutes indicative of triangular silver nanoplates (AgNPLs). The resulting solution was allowed to stir for an additional 10 minutes before it was covered and stored in the refrigerator 4° C. overnight before use. The same procedure was employed to form silver nanospheres (AgNSs) and nanorods (AgNRs), with the volume of $NaBH_4$ reduced to 110 µL and 160 µL, respectively. In some examples, inductively coupled plasma mass spectrometry (ICP-MS) is used to determine the concentration of the AgNPs and TEM can be used to determine the diameter. In some additional examples, UV-Vis, DLS, and TEM can be used to determine changes in AgNP size distribution in the presence of $CN^-$. Also, ICP-MS analysis can performed of the hybrid lipid-coated AgNPs prepared within 1 week and longer to confirm no $Ag^+$ are present that could play a role in toxicity. These methods also can be used to evaluate the size, shape, and dispersion of the AgNPs in 10 mM PBS buffer pH 8 and fish water. TEM can be used to determine if membrane coverage results in "patchy" lipid layers on surface using positive and negative staining agents such as uranyl acetate. Infrared spectroscopy can be used to determine if the thiols are attached to the AgNP surface while zeta potential will assess the overall surface charge of the AgNPs.

SOA (1.1 µL of a 9.4 mM in $H_2O$) was added to citrate-capped AgNPs (1 mL of nanoparticles of O.D. 1.2 at $\lambda_{max}$ 705 nm in $H_2O$) in an Eppendorf, vortexed for 5 seconds, and allowed to incubate for 20 minutes at room temperature. This was followed by the addition of PC liposomes (10.4 µL of 0.32 mM in 10 mM sodium phosphate buffer pH 8), which were incubated with the Ag-SOA for 40 minutes at room temperature after 5 second vortex mixing. The PC liposomes were prepared using a solution of PC (100 µL of 3.3 mM $CHCl_3$), which was evaporated under a stream of $N_2$ as a thin film and placed under vacuum of 12 h to remove trace organic solvents. The film was then resuspended in 1 mL of 10 mM sodium phosphate buffer pH 8 and sonicated for 90 minutes until the solution is clear. Following the addition of the PC, thiol (1.4 µL of a 30 mM solution in ethanol) was added to the Ag-SOA-PC solution and incubated for a minimum of 30 minutes before use.

Long-term storage stability was examined by storing the solution in the dark over time at 4° C. and taking UV-Vis spectra at different times. To determine if the surface of the AgNPs were shielded from oxidation, a cyanide ($CN^-$) etch test was performed. $CN^-$ is used to oxidize metals such as $Au^0$ and $Ag^0$ to $Au^{III}$ or $Ag^I$ in the presence of $O_2$. In this example, a 1 mL solution of AgNPLs of optical density 1.2 was incubated with 20 µL of the 307 mM KCN in an Eppendorf. For varying the effect of NaCl on stability, the AgNPLs were incubated with NaCl to yield final concentration of 50 mM, 100 mM, and 150 mM. To vary the pH, 1 µL and 4 µL of 2 M HCl was added to adjust the pH to 5 and 2, respectively from an initial pH 7-8. To test the effect of membrane disrupting surfactants, samples were incubated with 20 µL 10 mM Tween®20 for a final concentration 0.2 mM. Samples were then placed under storage conditions and allowed to incubate for 24 hour. The percent change in the optical density or LSPR were monitored by taking a UV-Vis spectrum before and after $CN^-$, NaCl, pH, or Tween®20 treatment. The NaCl treatment embodiments can be used to mimic salt concentrations in biological and natural waters; disulfides and thiol species can be used to determine susceptibility to ligand exchange and thus potential $Ag^+$ release; biological proteins can be used to determine protein absorption on the nanoparticle surface and any effects on behavior and/or stability; and the pH can be varied to determine how shape and size changes at low and high pH.

Ag-OA-PC-HT nanoparticles were prepared by drop casting dilute solutions of nanoparticles onto carbon-coated (300 Å) Formvar films on copper grids. This was allowed to sit for 1 hour before excess sample is wicked off by with a piece of filter paper. Transmission electron micrographs were acquired on a Tecnai F-20 FEI microscope using a CCD detector at an acceleration voltage of 200 kV. Nanoparticle size and interparticle spacing were performed using ImageJ Software. Absorbance measurements were performed with an Ocean Optics USB2000 UV-visible spectrophotometer using a 1.0 cm path length quartz cell.

AgNPs are known to undergo oxidation and dissolution to $Ag^+$ ions. As such, the hybrid coatings discussed above are used to stabilize the AgNPs and prevent $Ag^+$ ion release. In addition, unlike other syntheses of lipid-coated nanoparticles where an excess of lipids is used during the coating process, these hybrid lipid-coated AgNP composites are prepared with minimal lipids that cover the surface of each nanoparticle of a given size and shape. This strategy minimizes the formation of "nanoparticle-free" liposomes reducing purification steps of the materials after synthesis.

In some embodiments, to approximate the number of lipids necessary to cover AgNPs in a given volume of stock solution, the number of nanoparticles per mL is determined. The number of Ag atoms ("Q") present in the stock solution can be determined, where the quantity of $AgNO_3$ used for synthesis is known. Assuming the reduction of $Ag^+$ to $Ag^0$ goes to 100% completion, using equation 1 (where "$N_a$" is Avogadro's number), "Q" is determined.

$$Q = (\text{mol } Ag^+)(N_a) \qquad \text{Eq. 1}$$

To determine the total number of $Ag^0$ atoms per nanoparticle of given size and shape, the number of $Ag^0$ atoms that can occupy a given nanoparticle volume is determined using equation 2, $$q_i = V_i * \left(\frac{\rho_{Ag}}{FW}\right)(N_a) \qquad \text{Eq. 2}$$

where $q_i$ is the number of atoms contained in one nanoparticle of a given volume (i=rod, sphere, triangle), $V_i$ is the volume of the nanoparticle shape, $\rho_{Ag}$ is the density of Ag (g/nm$^3$), and FW is the atomic weight of Ag (g/mol).

To determine the volume ($V_i$) and surface area ($SA_i$) of a nanoparticle irrespective of nanoparticle shape the following equations are used, $$V_{sphere} = \frac{4}{3}\pi\left(\frac{D}{2}\right)^3 \quad \text{Eq. 3}$$

$$SA_{sphere} = 4\pi\left(\frac{D}{2}\right)^2 \quad \text{Eq. 4}$$

$$V_{rod} = \frac{4}{3}\pi\left(\frac{D}{2}\right)^3 + (L-D)\left(\pi\left(\frac{D}{2}\right)^2\right) \quad \text{Eq. 5}$$

$$SA_{rod} = 4\pi\left(\frac{D}{2}\right)^2 + (L-D)(\pi D) \quad \text{Eq. 6}$$

$$V_{triangle} = d\left(\frac{L}{2}(L*\text{Sin}(60))\right) \quad \text{Eq. 7}$$

$$SA_{triangle} = L((L*\text{Sin}(60)) + 3d) \quad \text{Eq. 8}$$

To determine the number of surface atoms ("B") available on a given nanoparticle, the total surface area of each nanoparticle is divided by the circular area occupied by each $Ag^0$ with a metallic diameter ("$D_{Ag}$"). Since the atomic packing of an FCC crystal structure is not perfect, an adjustment is made to the total number of $Ag^0$ atoms that could optimally fit within the calculated surface area using the packing efficiency ($E_{FCC}$) of an FCC crystal structure of 0.7405 using equation 9.

$$B = E_{FCC}\left(\frac{SA_i}{\pi\left(\frac{D_{Ag}}{2}\right)^2}\right) \quad \text{Eq. 9}$$

Furthermore, since embodiments of the methods of making nanoparticles disclosed herein can produce AgNPs where other shapes are obtained, the number of surface atoms available to account for the presence of other shapes can be determined to provide fully covered nanoparticles by determining the total number of entities present in solution and the number of each constituent shape. For example, if the percent shape composition of the final batch of nanoparticles ($P_{sphere}$, $P_{rod}$, and $P_{triangle}$), the number of constituent particles ($N_{sphere}$, $N_{rod}$, and $N_{triangle}$), the quantity of silver atoms required to form each constituent particle ($q_{sphere}$, $q_{rod}$, and $q_{triangle}$), and the total number of silver atoms (Q) are determined, then the relationship between total number of nanoparticles ($N_T$) is as follows:

$$N_{sphere} = N_T * P_{sphere} \quad \text{Eq. 10}$$

$$N_{rod} = N_T * P_{rod} \quad \text{Eq. 11}$$

$$N_{triangle} = N_T * P_{triangle} \quad \text{Eq. 12}$$

Therefore, the total number of atoms is, $$Q = N_{sphere}*q_{sphere} + N_{rod}*q_{rod} + N_{triangle}*q_{triangle} \quad \text{Eq. 13}$$

We can then substitute out the known relations, $$Q = P_{sphere}*N_T*q_{sphere} + P_{rod}*N_T*q_{rod} + P_{triangle}*N_T*q_{triangle} \quad \text{Eq. 14}$$

Which then can be rearranged to the following, $$N_T = \frac{Q}{P_{sphere}*q_{sphere} + P_{rod}*q_{rod} + P_{triangle}*q_{triangle}} \quad \text{Eq. 15}$$

For example, for a spherical nanoparticle of roughly 27 nm diameter, an estimated 3300 molecules of PC can be used for a single inner leaflet of lipids around the AgNP core (based on a PC head group size of 69.4 $Å^2$). In some embodiments, a 1 nm water cushion can separate the lipids from the surface, therefore, an additional 4350 lipids are used to create an outer leaflet of lipids. Similar calculations for AgNRs of length 40 nm and width 19 nm, as well as AgNPLs of face-width 29 nm and 18 nm thickness also are performed, yielding inner leaflet PC molecule counts of ~3440 and ~4581, for rods and triangles respectively, and outer counts of ~3306 and ~4497 molecules, for rods and triangles respectively.

For a 1 mL solution of blue AgNPs, with shape distributions of 50%, 45%, and 15%, respectively for spheres, rods, and triangles, a total of 1.43 nmol of lipids are used for complete coverage. To account for this, any inefficiency in transfer of liposomes to the silver surface and differences due to shape, a total of 3.36 nmol was used and it was determined that this provided complete coverage as demonstrated by cyanide stability (vide infra).

Using the estimated number of lipids determined, HBM-coated AgNPs are prepared. In some embodiments, a ratio of PC:thiol was determined and used to determine that certain hybrid AgNP embodiments are comprised of an inner leaflet of thiol and an outer leaflet of PC and sodium oleate. Without being limited to a particular theory, it currently is believed that this configuration arises from the excess thiol addition to the system, which results in complete surface coverage and displacement of oleate (OA) moieties which initially forms a weaker Ag—OH bond, which can be observed experimentally where Ag-OA nanoparticles are observed to etch slowly in the presence of aqueous KCN, whereas Ag-OA-HT nanoparticle composites are almost completely stability.

Example 6

Figure 19A:
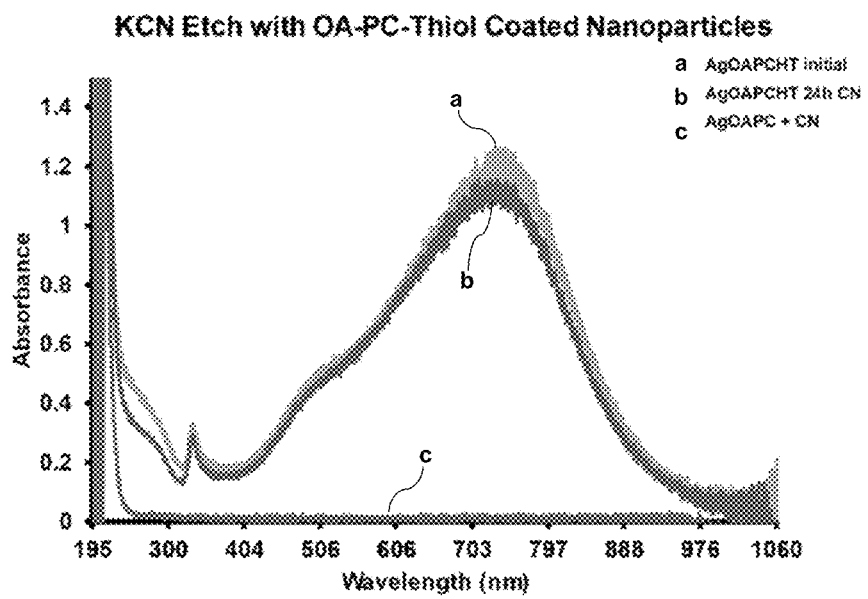
FIGS. 19A and 19B are UV-vis spectra of a triangular Ag-SOA-PC-HT nanoparticle composite (FIG. 19A) and a triangular Ag-SOA-HT nanoparticle composite (FIG. 19B) before and after the addition of KCN (lines "a" and "b," respectively), and after treatment with KCN in 10 mM sodium phosphate buffer pH 8 (line "c").
Figure 19B:
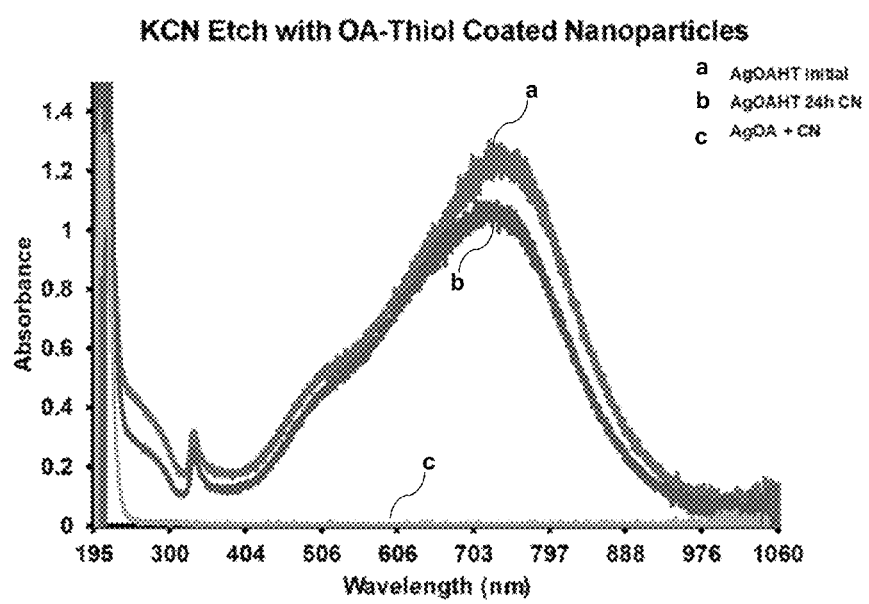

In this example, AgNP composite stability was evaluated with the cyanide etching procedure described above. An immediate decrease in the LSPR band was observed upon the addition of $CN^-$ to Ag-SOA-PC with no thiol ligands (FIG. 19A, line c), while no significant decrease in LSPR was observed over 24 hours with samples containing PC and thiols, Ag-SOA-PC-HT (FIG. 19A, lines "a" and "b"). However, a notably larger change in LSPR peak is observed when PC is removed from the configuration to provide Ag-SOA-HT (FIG. 19B). The lack of change in the LSPR band indicates that the AgNP surface is completely covered by lipids, thiols, and SOA molecules in a tightly packed arrangement such that $CN^-$ ions are not able to penetrate the bilayer and etch the AgNP surface and is similar to that observed with spherical hybrid lipid-coated AuNPs. The $CN^-$ etch studies further demonstrate that the design strategy comprised of using thiol anchors is versatile and can be used to tune and stabilize membranes on silver and gold nanoparticle supports on a variety of shapes and sizes.

Additionally, samples of nanoparticles were prepared by incubating Ag-SOA and Ag-SOA-PC nanoparticles with 41 µM DT, HT, and PT for a minimum of 30 minutes before $CN^-$ was added to the samples. UV-Vis spectra recorded of Ag-OA-thiol and Ag-SOA-PC-thiol samples before and after $CN^-$ addition showed a significant change in the LSPR (>18%) and OD (>67%) of nanoparticles containing PT (FIGS. 20A and 20B), whereas, minimal change was observed for samples containing HT (% change LSPR <7, % change <17) and DT (% change LSPR <7, % change <17)

Figure 20A:
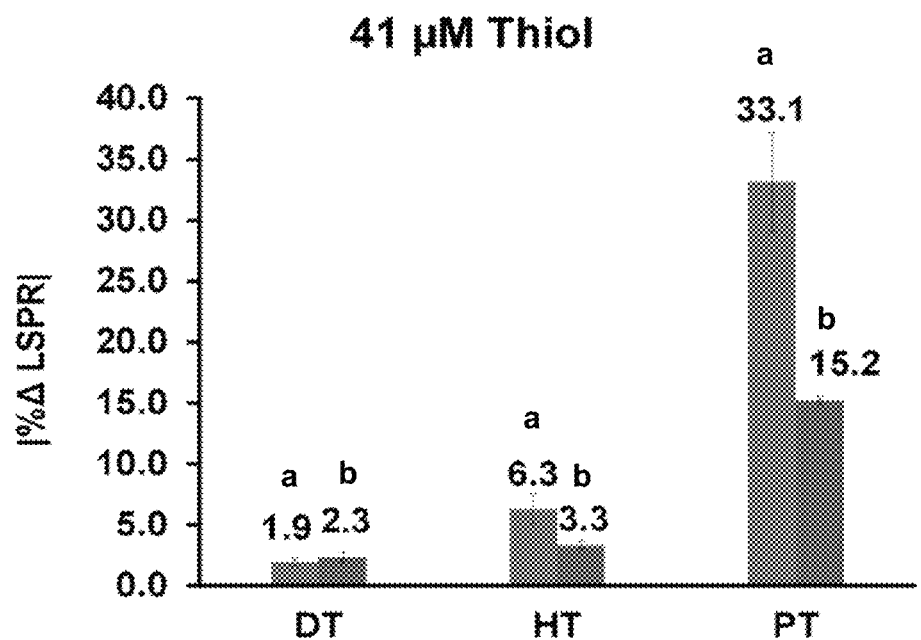
FIGS. 20A and 20B are graphs showing the representative % change in the LSPR band (FIG. 20A) and the optical density (OD) band (FIG. 20B) of a Ag-SOA-thiol nanoparticle (bars labeled with "a") and a Ag-SOA-PC-thiol coated nanoparticle composite (bars labeled with "b") 24 hours after the addition of 20 µL of 307 mM KCN in 10 mM sodium phosphate buffer pH 8; DT=decanethiol, HT=hexanethiol, and PT=propanethiol.
Figure 20B:
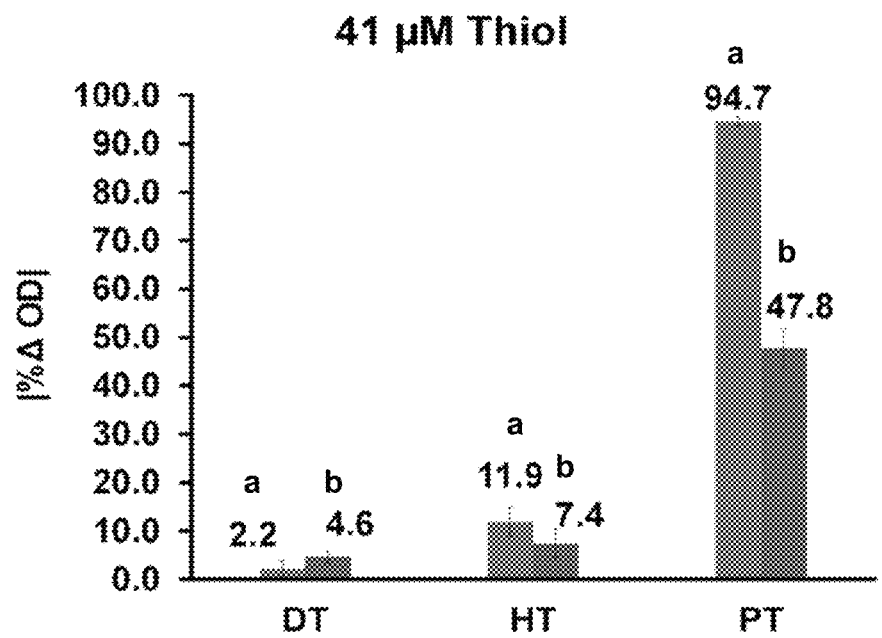

(FIGS. 20A and 20B). In addition, based on the shift in the LSPR and the decrease in the OD, overall the Ag-OA-thiol nanoparticles were found to be less stable than the Ag-SOA-PC-thiol nanoparticles demonstrating that the hybrid bilayer protects the surface from strong oxidants and keeps them stable in aqueous media. It currently is believed that in some embodiments the long chain hydrophobic thiols provide improved stability by helping to anchor the membranes close to the gold surface in a tight packing arrangement. A ranking of the AgNP stability in the presence of $CN^-$ with thiols of varying chain length was determined for some embodiments to be as follows: DT>HT>PT.

Figure 21A:
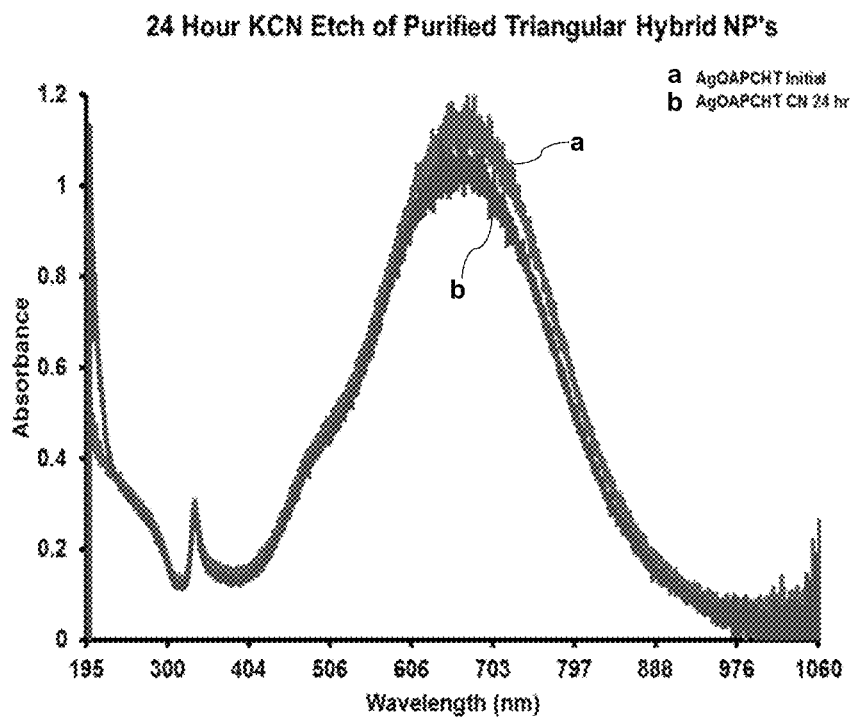
FIGS. 21A and 21B are UV spectra and a % change plot, respectively, of silver nanoparticle composite embodiments, which were subsequently purified, and subject to etching for 24 hours using 20 µL of 307 mM KCN in 10 mM sodium phosphate buffer pH 8, with a final hexanethiol concentration of 41 µM.
Figure 21B:
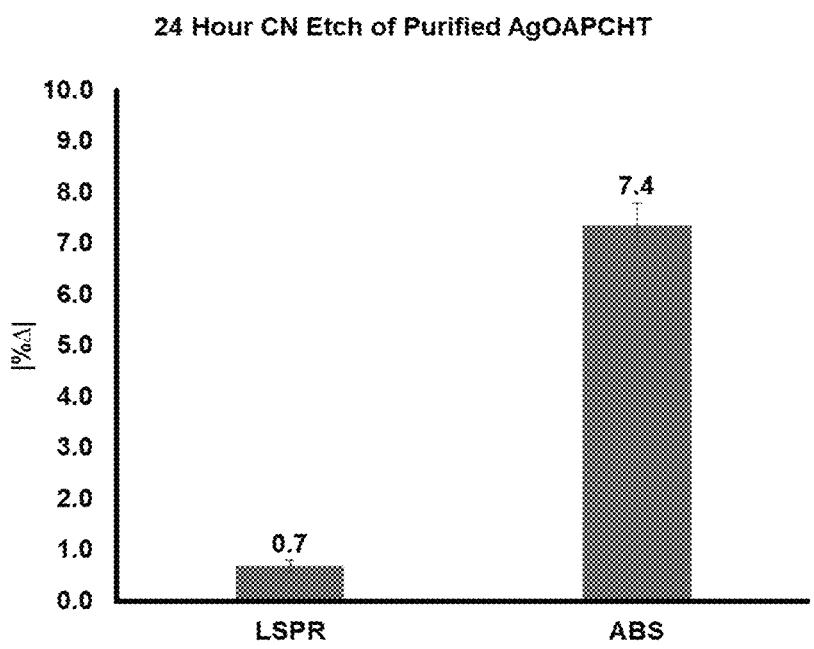

Once KCN stability had been confirmed, the HT variation was selected to examine the stability of the hybrid motif after being subject to a purification process, removing any excess thiols and reagents that may be influencing the etching profile. Additionally, purification improves the platforms viability for future applications sensitive to the reagents used in synthesis. Each sample being purified was combined with 10 μL of 10 mM Tween®20 solution per 1 mL of hybrid nanoparticle stock, and allowed 10 minutes to incubate. The prepared solution was then subject to ultra-centrifugation at 4700 rpm, using a Vivaspin 20 centrifuge filter, washing three times using 10 mM sodium phosphate buffer, followed by two washes using nanopure water. FIGS. 21A and 21B shows the KCN stability of the purified hybrid system.

Figure 22:
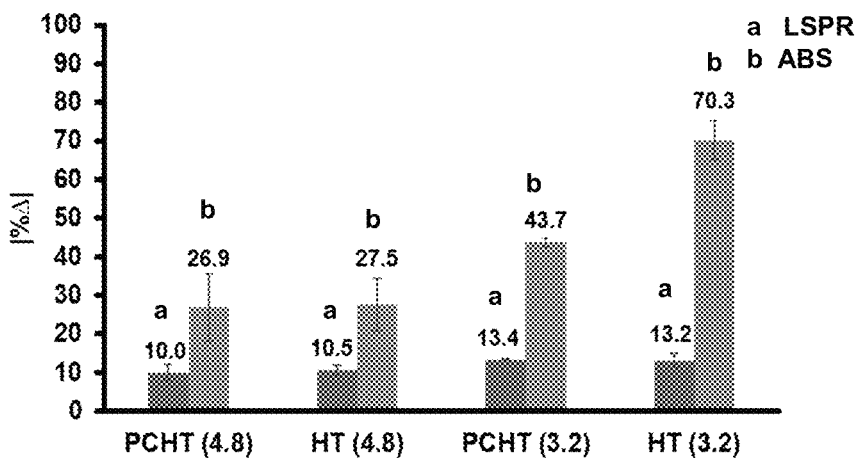
FIG. 22 is a graph of absolute value of the % change in the LSPR (bars labeled "a") and absorbance (bars labeled "b") for a Ag-SOA-PC-HT nanoparticle composite and a Ag-SOA-HT nanoparticle composite exposed to KCN for 1 week, and wherein the two sample-sets were synthesized using 4.8 nmol HT and 3.2 nmol HT.

The minimal amount of thiol required for complete coverage for a 1 mL sample was determined to be 4.8 nmol, based off the geometric calculations discussed in Example 5. To verify, a CN etch stability study was performed on two sets of thiol-only and PC-thiol hybrid variants, synthesized using 4.8 nmol of HT and 3.2 nmol of HT (FIG. 22).

Figure 23A:
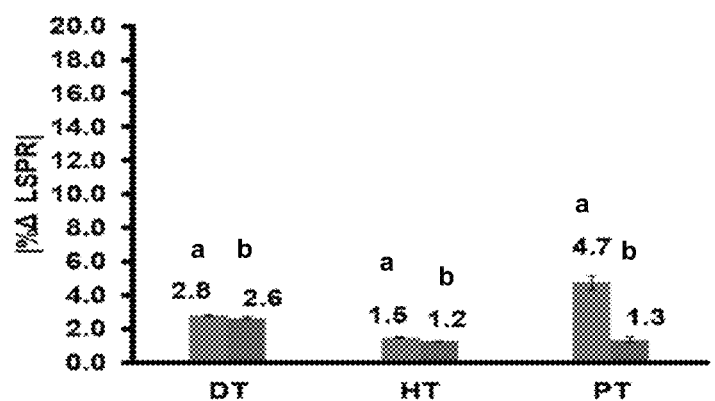
FIGS. 23A and 23B are graphs of absolute value of the % change in the LSPR band of Ag-SOA-thiol and Ag-SOA-PC-thiol composites at 24 hours (FIG. 23A) and after 21 days (FIG. 23B) of storage, wherein DT=decanethiol, HT=hexanethiol, and PT=propanethiol.
Figure 23B:
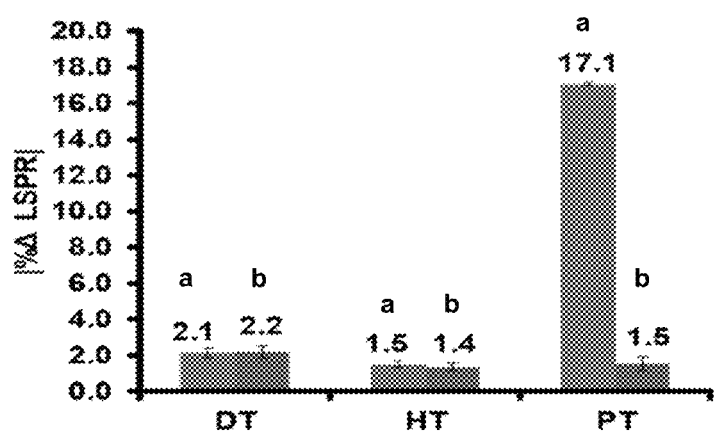
Figure 24A:
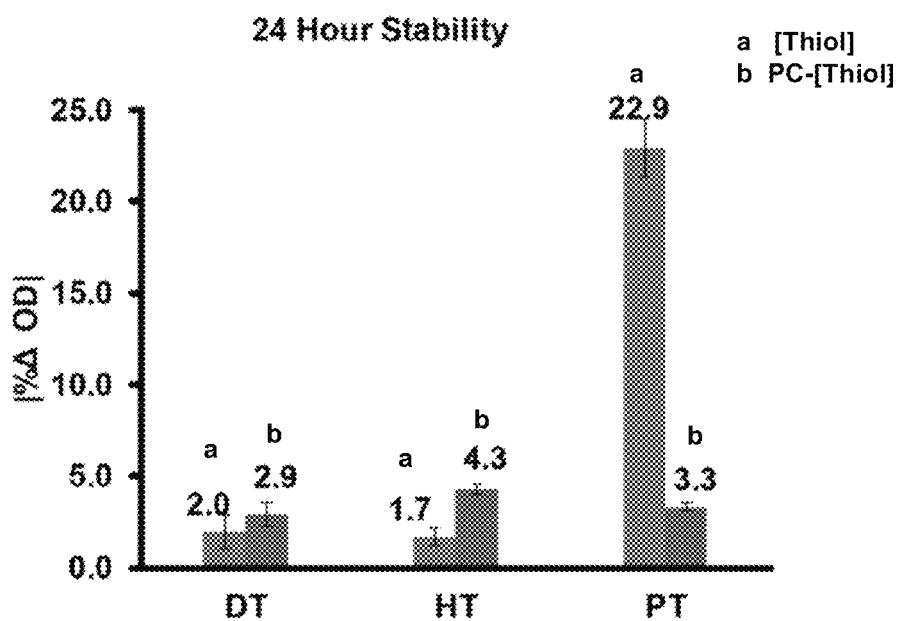
FIGS. 24A and 24B are graphs of absolute value of the % change in the OD band of Ag-SOA-thiol and Ag-SOA-PC-thiol composites at 24 hours (FIG. 23A) and after 21 days (FIG. 23B) of storage, wherein DT=decanethiol, HT=hexanethiol, and PT=propanethiol.
Figure 24B:
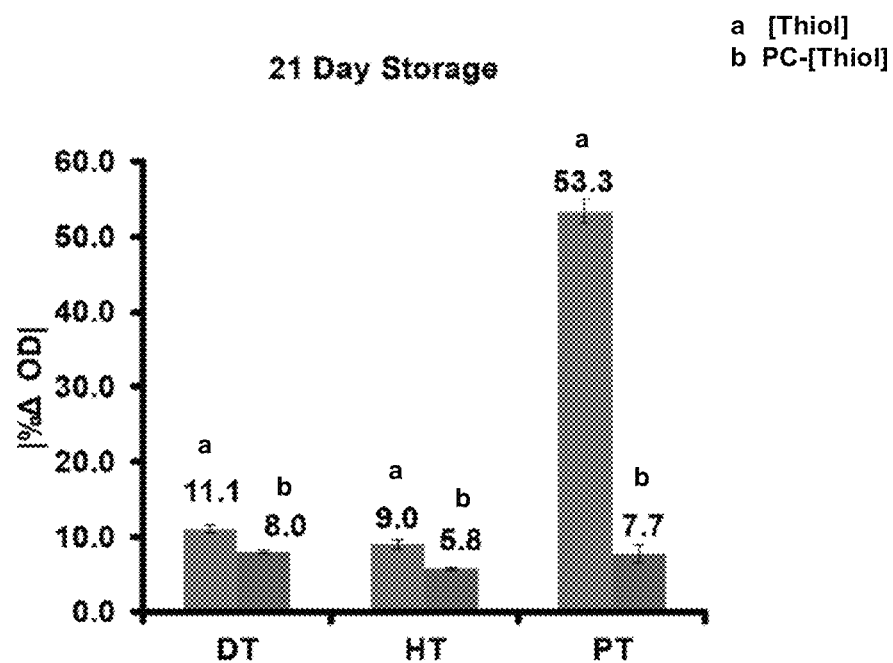

At higher concentrations of thiol minimal aggregation is observed and the Ag-SOA-PC-HT and Ag-SOA-PC-DT remain stable to $CN^-$. A noticeable change in LSPR and OD was observed with Ag-SOA-PT nanoparticles at after 24 h and after 21 days of storage (FIGS. 23A and 23B, respectively). This significant drop in OD and LSPR indicates loss of nanoparticle stability with the short-chained thiols. This observation is consistent with the noticeable dark precipitate observed in the vial after 21 days of storage. Only a 9-11% drop decrease in OD and minimal shift in SPR was observed for the Ag-SOA-HT and Ag-SOA-DT samples. Overall, in the presence of the PC, the Au-SOA-PC-thiol nanoparticles remained unaggregated and stable even after 21 days of storage (FIGS. 24A and 24B). The lack of change in the SPR band suggests that the PC bilayer membrane is surrounding the nanoparticle where the polar head groups are facing the aqueous environment and are protecting the nanoparticle core from oxidation enhancing their long-term stability.

Figure 25A:
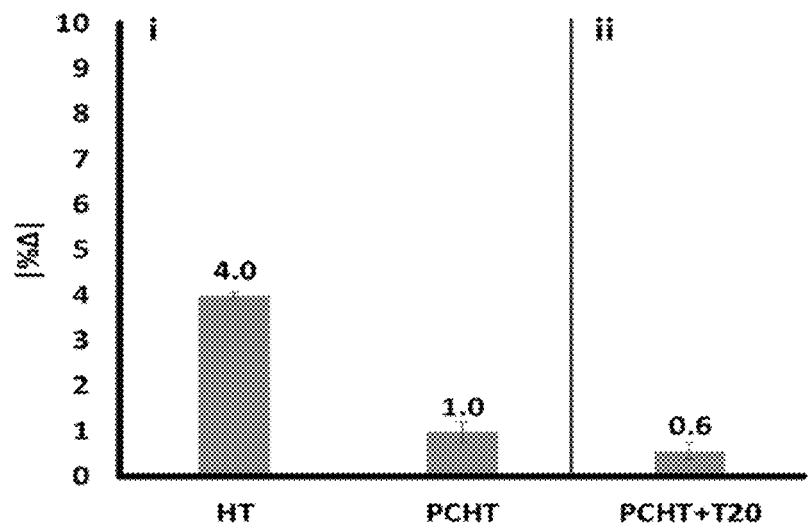
FIGS. 25A and 25B are graphs showing a comparison of the percent change in the absorbance of a Ag-OA-HT nanoparticle composite, a Ag-OA-PC-HT nanoparticle composite, and a Ag-OA-PC-HT nanoparticle composite with Tween®20 (FIG. 25A) and a Ag-OA-PT nanoparticle composite, a Ag-OA-PC-PT nanoparticle composite, and a Ag-OA-PC-PT nanoparticle composite with Tween®20 (FIG. 25B).
Figure 25B:
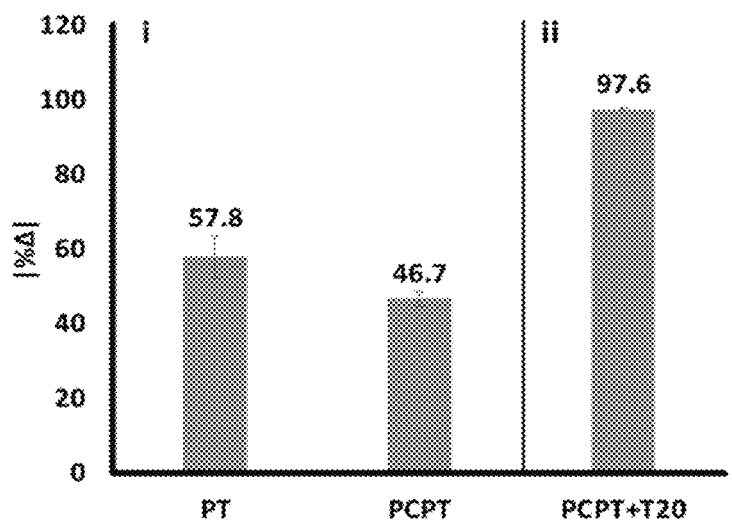

To test the robustness of the hybrid lipid-coated AgNPs, samples were exposed to membrane disrupting surfactants, chlorides, disulfides, thiolates, and varying pH conditions. For example, a 1 mL solution of Ag-OA-PC-thiol nanoparticle samples were exposed to Tween®20, a well-known membrane disrupting agent. After a 30 minute incubation period, each sample's UV spectra was collected, and then 20 μL of 307 mM KCN was added to each sample. To ensure that liposome disruption occurred, four times the critical micelle concentration (CMC) of Tween®20 was added to each sample (resulting PC:TWEEN®20 ratio is 1:15), which resulted in a final concentration of 0.2 mM per sample (4×60 mg/L). Minimal change in the ABS (<6%) was observed upon the addition of TWEEN®20 long-chain thiol, HT, and CN over a 1 week period (FIG. 25A), while a significant change (>24%) was observed for samples containing PT (FIG. 25B). This suggests that even in the presence of membrane disrupting surfactants hybrids formed with long chained thiols (HT and DT) are protected from $CN^-$ etch compared to those short-chained thiols, PT. The observed difference in etch resistance for PT suggests that it tail unable to fully interdigitate into the encapsulating bilayer or monolayer, resulting in a less densely packed lipid layer that surfactant molecules are able to disrupt. Additional results are illustrated in FIGS. 26A and 26B.

Figure 27A:
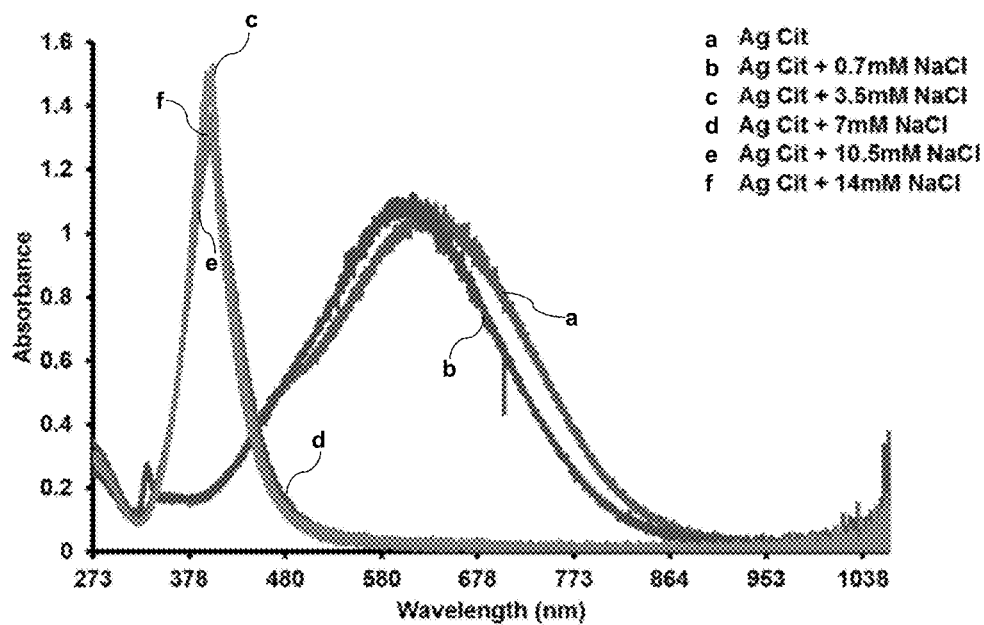
FIGS. 27A and 27B are UV-spectra of bare Ag-citrate nanoparticles etching in the presence of low concentrations of NaCl ranging from 0.7 mM to 14 mM (FIG. 27A) and a Ag-OA-PC-HT composite in the presence of significantly higher concentrations of NaCl, ranging from 50 mM to 150 mM (FIG. 27B).
Figure 27B:
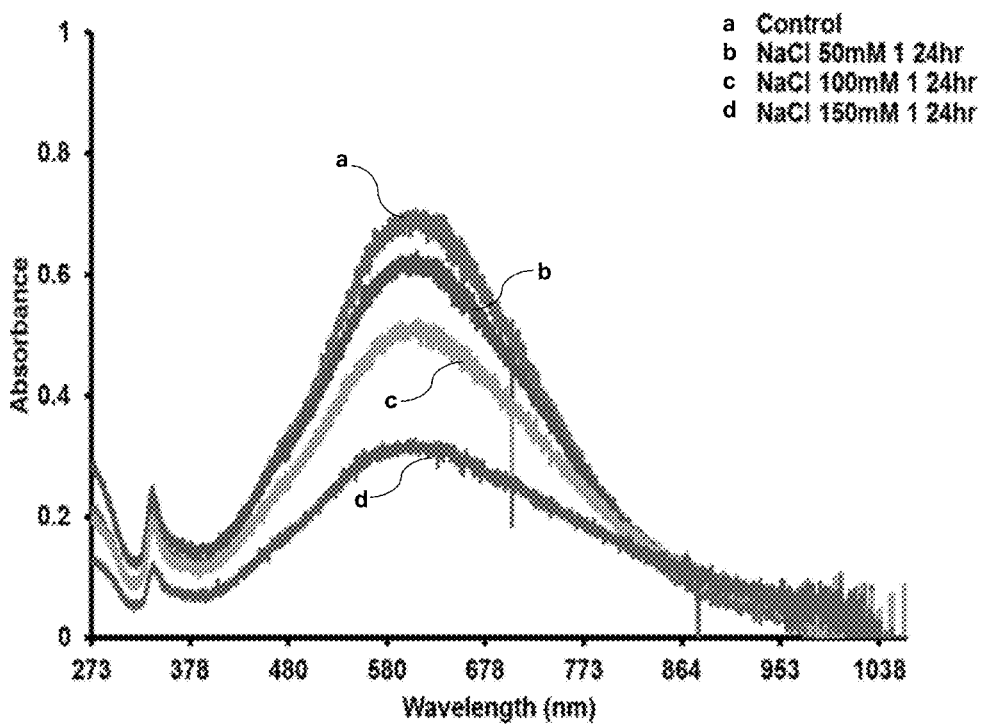

Hybrid lipid-coated AgNPs were exposed to varying NaCl and $CaCl_2$ concentrations and changes in the LSPR and the OD monitored at after 1 and 24 hour. When exposed to increasing concentrations of NaCl (50 mM-150 mM), the hybrid nanoparticle system shows a negligible change in LSPR (<1%), with a moderate decrease in OD proportional to the concentration NaCl (FIG. 27B). These observations differ significantly from that of bare citrate-capped AgNPs, which readily etch in the presence of small concentrations of NaCl (>0.7 mm), resulting in rapid and dramatic changes to both the LSPR and OD (FIG. 27A). These changes are normally due to the nanoparticle shape and concentration being changed as $Cl^-$ ions oxidize the exposed surface $Ag^0$ atoms to form $AgCl_2$.

AgOAPCHT samples showed a more pronounced LSPR and OD change when exposed to $CaCl_2$ (FIG. 28), but maintained a stable LSPR when exposed to low concentrations.

Example 7

In this example, the stability of hybrid lipid-coated AgNPs in real exposure conditions was evaluated. Samples were exposed to varying NaCl, pH, and to disulfides and changes in the LSPR monitored. Upon exposing the Ag-SOA-PC-HT to 150 mM of NaCl a 50% decrease in O.D. is observed indicating aggregation (FIG. 29A). However, at low concentrations of NaCl (50 mM) very minimal aggregation is observed (FIG. 29B). When the pH of the solution is lowered to 2, the Ag-SOA-PC-HT aggregate as indicated by a drop in the OD and a shift in LSPR band (FIG. 29B). At pH 5, there is also a decrease in the OD but it is not as significant as that observed at pH 2. In addition, exposure to 100 mM excess of $CaCl_2$ and glutathione also showed aggregation. In all cases, the nanoparticles aggregate but no evidence of a shape change is observed.

Example 8

In this example, zebrafish embryos (*Danio rerio*) are used as an integrated sensing and amplification system that provided the ability to non-invasively examine nanoparticle behavior, providing the power of whole-animal investigations with the convenience of cell culture. Exposures are conducted in 96-well plates using intact organisms that have functional homeostatic feedback mechanisms and intercellular signaling. Embryonic zebrafish are obtained from a 5D strain of zebrafish (*Danio rerio*) reared in the Sinnhuber Aquatic Research Laboratory (SARL) at OSU. Adults are kept at standard laboratory conditions of 28° C. on a 14 h light/10 h dark photoperiod. Embryos are collected from group spawns and staged for evaluation. Embryos (6 hpf) are dechorionated prior to waterborne exposure to avoid barrier effects posed by the chorion (egg membrane). Since zebrafish embryos are transparent, simple microscopic evaluations can be used to non-invasively observe the development and assess for morphological or behavioral alterations throughout the exposure period. The methods for waterborne-exposed embryos are conducted and control and nanomaterial-exposed groups are statistically compared using one-way ANOVA (Sigma Stat, SPSS Inc., Chicago, Ill.). Kruskal-Wallis Analysis of Variance on Ranks is used if the data violate normality or equal variance assumptions. The lethal concentration to cause 50% embryonic mortality (LC50) is calculated using probit and sigmoidal regression analyses, and the LOAEL is calculated using an ANOVA (SPSS Inc., Chicago, Ill.). Uptake of AgNPs is quantified and biodistribution is determined using HSI. In vivo localization is determined by the location of the spectral signatures when compared to a spectral library and non-exposed control fish.

Additionally, small-scale nanocosms with organisms from multiple trophic levels are used to determine the impact of nanoparticle embodiments described herein under different exposure scenarios. Nanocosms comprised of algae (*Chlamydomonas reinhardtii*) and bacteria (*Escherichia coli*) are compared to increasingly complex nanocosms comprised of algae, bacteria, predatory invertebrates (*Daphnia magna*), and developing vertebrates (*Danio rerio*). Test species are selected to represent a broad spectrum of trophic levels and are accepted as good model organisms for aquatic toxicity testing, particularly for nanoparticles. *C. reinhardtii* and *E. coli* are chosen to represent primary producers and decomposers, respectively. While bacteria and plankton compete with each other for resources, both serve as food for the secondary consumer, *D. magna*, which are small aquatic crustaceans ubiquitous in freshwater lotic environments and are included as a primary grazer of the microorganisms. *D. magna* are sensitive to chemical stressors and have utilized as an indicator species for assessing aquatic contamination. Embryonic zebrafish are selected as a developing vertebrate model due to their rapid development, relatively high sensitivity to anthropogenic contaminants during development, transparency for visual observations, and are well-studied sublethal endpoints elicited from NP exposures.

Nanocosm studies of controls, such as $ZnO$, $TiO_2$, Cu, and CuO NPs, are compared to AgNP composite embodiments disclosed herein and their exposures in nanocosms comprised of algae and bacteria to increasingly complex nanocosms containing predatory invertebrates and developing vertebrates are evaluated. Each nanocosm is exposed to 70 nm of the AgNPs composite embodiments. Comparative nanoparticles, such as AgNPs with a polyethylene glycol coating (PEG-AgNP) or silica (Si—AgNP), or aminated silica-coated AgNP (Ami-Si—AgNP) as described in Environ. Sci.: Nano, 2017, 4, 359, can be used investigate the relative influence of surface charge, composition and dissolution on organismal uptake and toxicity. As described in Environ. Sci.: Nano, 2017, 4, 359, all three comparative AgNPs have significantly higher $Ag^+$ release into solution when organisms are present than is measured in the same media without organism's present (see FIG. 3 of this manuscript; FIG. 3 is incorporated herein by reference). PEG-AgNPs had the highest overall toxicity in all three nanocosm scenarios, followed by Si-AgNPs, and lastly Ami-Si-AgNPs. Toxicity correlated with the amount of $Ag^+$ measured in the exposure media and the amount taken up by the organisms. These results help establish that surface functionalization plays a role in determining dissolution, uptake, and toxicity of AgNPs. Increasing trophic complexity decreased organismal susceptibility under the same AgNP concentration exposures, likely due to the change in bioavailable $Ag^+$ that each organism experienced. These results establish that a nanocosm assay is effective in determining differential impacts of AgNPs and thus can be used with nanoparticle composite embodiments disclosed herein to assess activity and viability of these nanoparticle composite embodiments.

Example 9

Fluorophore-labeled oligomer specific antibodies also can be used in certain embodiments. $A\beta$ conformer specific antibodies will only detect oligomer species and not larger $A\beta$ species such as fibrils. The oligomer antibodies are conjugated to near infrared fluorescent dyes and are used in binding studies to investigate how the size influences membrane disruption. Fluorescently-tagged $A\beta$ oligomers of different sizes facilitate identifying which size oligomer plays a more significant role in membrane disruption and neurotoxicity.

Figure 30:
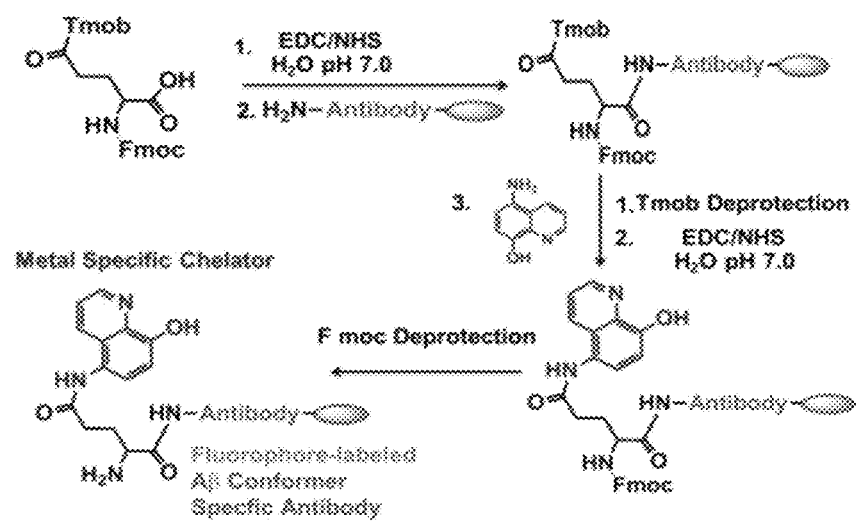
FIG. 30 is a schematic illustration of the preparation of Aβ conformer specific sensors.

The fluorophore-labeled oligomer specific antibody is coupled to a glutamine amino acid ligand scaffold containing a metal specific chelator (FIG. 30). For example, the amino derivative (5-amino-8-hydroxyquinoline) of clioquinol, a known chelator of $Cu^{2+}$, can be employed to detect Cu-$A\beta$ oligomers. Using multi-fluorophore-labeled oligomer specific antibodies coupled to metal specific chelators a multi-spectral response can be obtained that allows quantitative differentiation of multi-metal $A\beta$ conformer species (Cu-$A\beta$, Fe-$A\beta$, Zn-$A\beta$) using fluorescence spectroscopy.

To establish the binding affinity of different size $A\beta$ conformers and metallated-$A\beta$ derivatives, studies of stabilities and preferences to PC-coated AuNPs are performed. Assays are performed in 3 different types of matrices (buffer, CSF and human plasma) containing nominal concentrations of freshly prepared $A\beta$ oligomers of different sizes (4.5-50 kDa) and metallated-$A\beta$ (Cu, Zn and Fe) derivatives under varying pH 6-8 and ionic strength at 37° C. The % change in the anisotropy or LSPR band is related to amount of $A\beta$ binding to the AuNP. A binding curve using the change in anisotropy under varying concentrations of $A\beta$ conformer species is then established. A fit of the curve and the equation below is used to calculate the dissociation constant ($k_d$).

$$\frac{1}{r-rb} = \left(\frac{Kd}{rb-rf}\right)\frac{1}{PT} + \left(\frac{1}{rb-rf}\right)$$

With respect to this equation, $r_b$ is the bound anisotropy, $r_f$ is the anisotropy of the free fluorophore-labeled species and $P_T$ is the total protein concentration. A well-established Pierce 660 protein assay also is used to determine the amount of soluble protein unbound to Au-SOA-PC-HT nanoparticles to validate the nanosensor effectiveness.

A horseradish peroxidase (HRP)/luminol chemiluminescence lipid peroxidation assay is used to determine if metallated-$A\beta$ generate $H_2O_2$ to induce lipid peroxidation. This assay is performed in the presence of $A\beta$ conformers of different sizes and metallated-$A\beta$ in the presence of PC-coated AuNPs. To determine if there are changes in membrane integrity cyanide etch studies can be conducted. Alternatively, a membrane leakage dye (1,6-diphenylhexatriene, (DPH)) can be used as supporting evidence of membrane permeability or pore formation. DPH is a fluorescent dye in hydrophobic environments and non-fluorescent in aqueous media. A decrease in fluorescence as the dye leaks indicates loss of membrane integrity or pore formation. Atomic force microscopy will confirm if a pore forms. In the case of carpeting or surface binding interactions with membranes minimal or no cyanide etch or dye leakage is expected as these types of interactions are proposed to have minimal disruptions on membrane integrity. A lack of DPH fluorescence will confirm this. These embodiments can be used to identify which type of Aβ species has the most pronounced effect on the membrane integrity and the mechanism by which they do so.

Example 10

Figure 31:
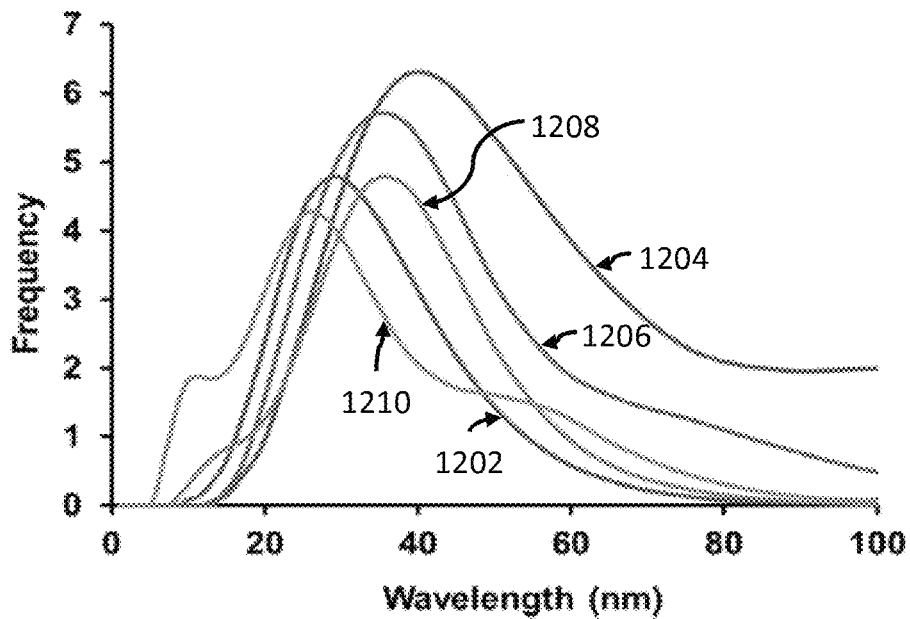
FIG. 31 is a graph of frequency as a function of wavelength (nm) showing that the hydrodynamic radius of nanoparticle composites described herein, such as those illustrated in FIG. 12, can be tuned by modifying the membrane composition surrounding the nanoparticle core of the nanoparticle composite.
Figure 32:
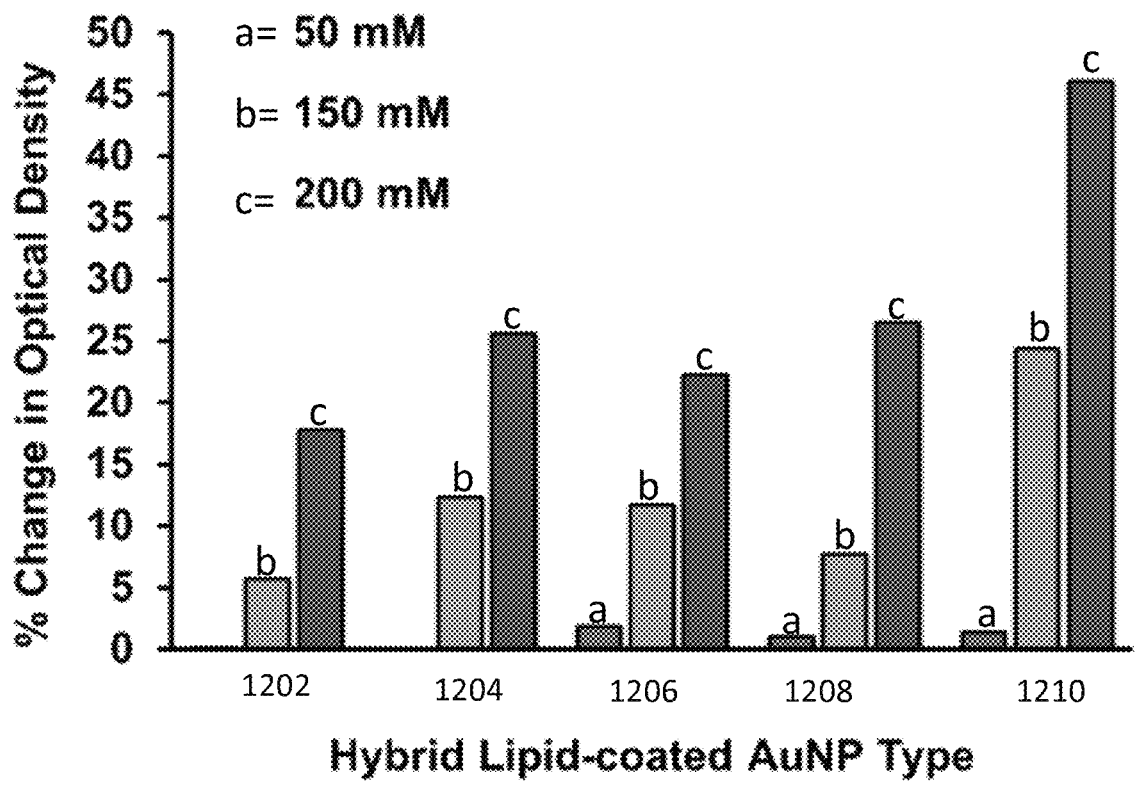
FIG. 32 is a graph of percent change in optical density for different hybrid lipid-coated nanoparticle composites illustrating the stability of the nanoparticle composites under different physiological salt concentrations (50 mM (a), 150 mM (b), and 200 nM (c)); embodiments utilizing membrane components 1202, 1204, 1206, and 1208 as illustrated in FIG. 12 were evaluated.
Figure 33:
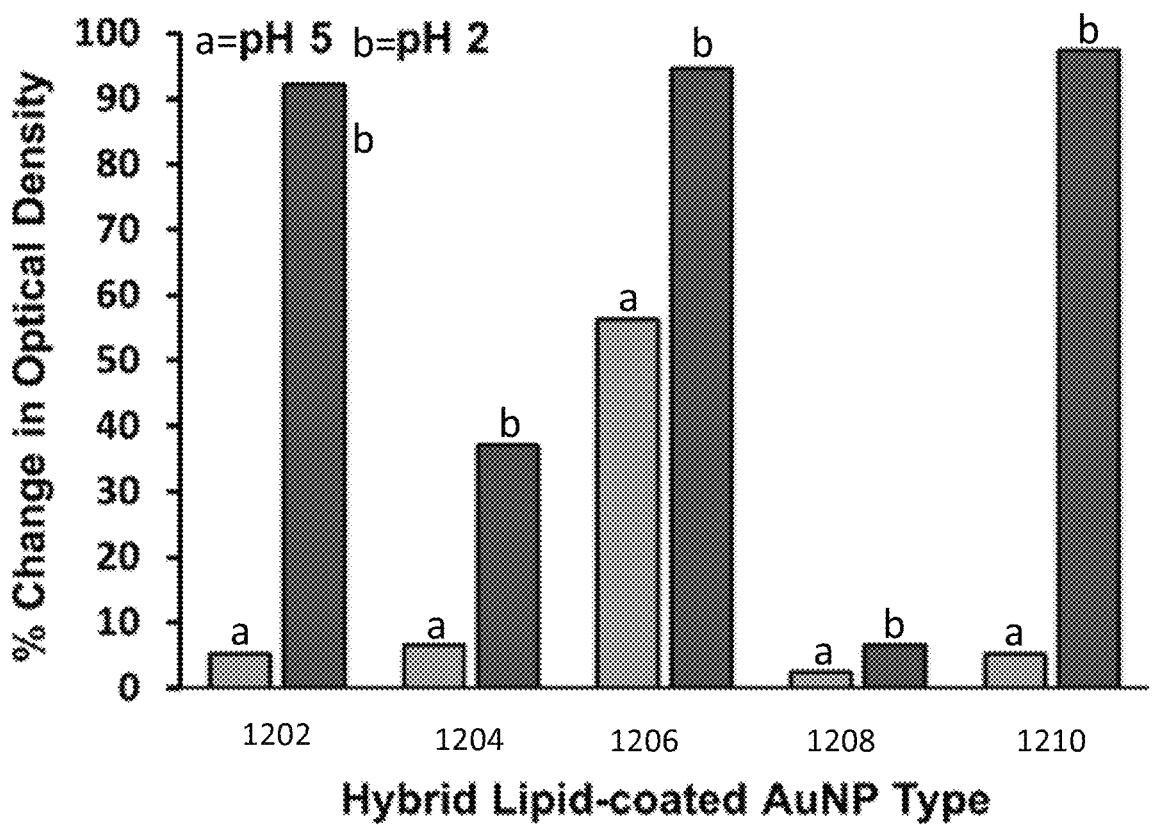
FIG. 33 is a graph of percent change in optical density for different hybrid lipid-coated nanoparticle composites illustrating the effect of pH (pH 5 (a) and pH 2 (b)) on the nanoparticle composites' stability; embodiments utilizing membrane components 1202, 1204, 1206, and 1208 as illustrated in FIG. 12 were evaluated.
Figure 34:
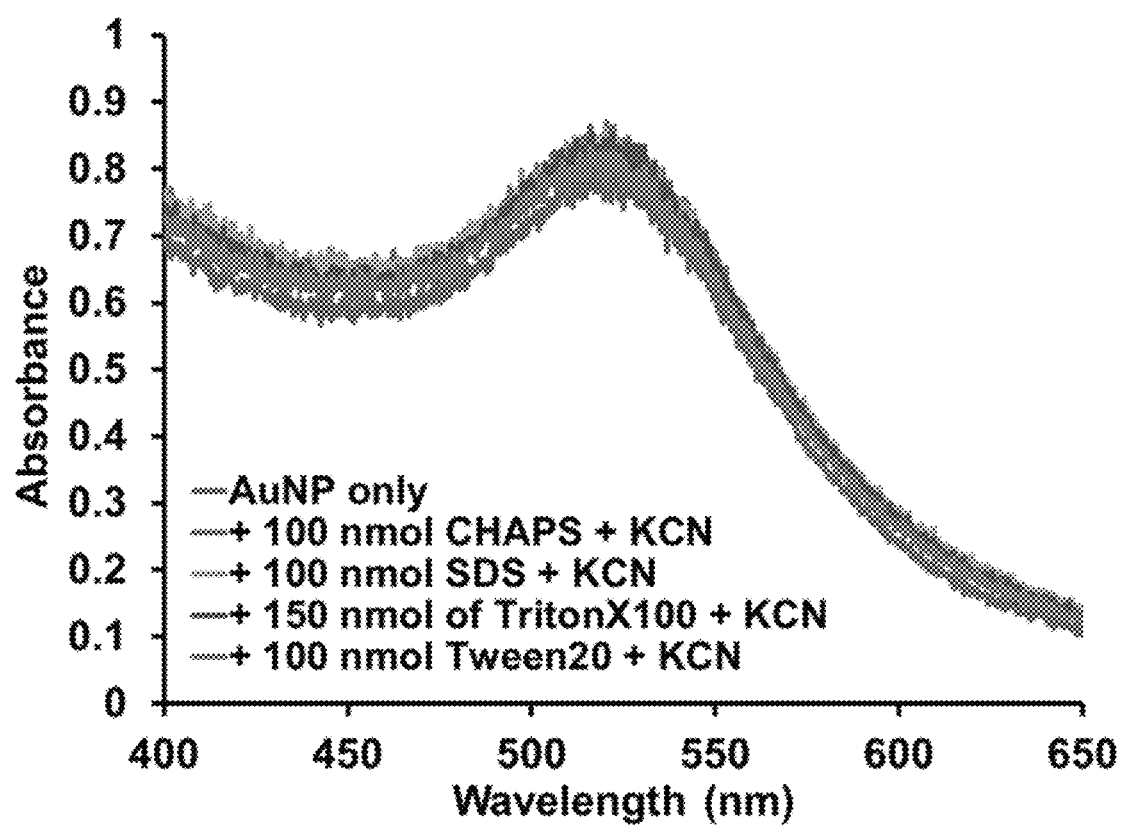
FIG. 34 is a graph of absorbance as a function of wavelength (nm) showing the effect on nanoparticle composites using cyanide etching in the presence of membrane disrupting agents.
Figures 35A, 35B, 35C:
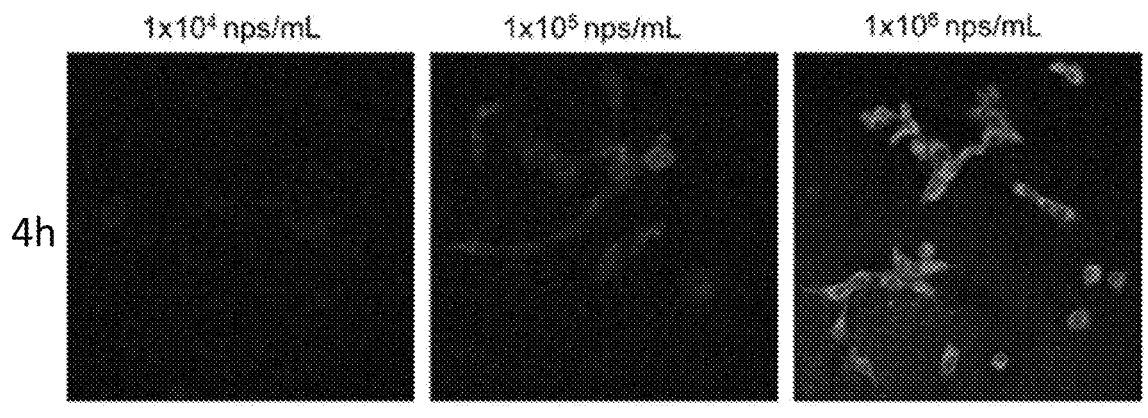
FIGS. 35A-35F are confocal microscopy images showing results obtained from analyzing the uptake of hybrid lipid-coated nanoparticle composites comprising rhodamine dyes; the results illustrate that the nanoparticle composites can readily be taken up in cells.
Figures 35D, 35E, 35F:
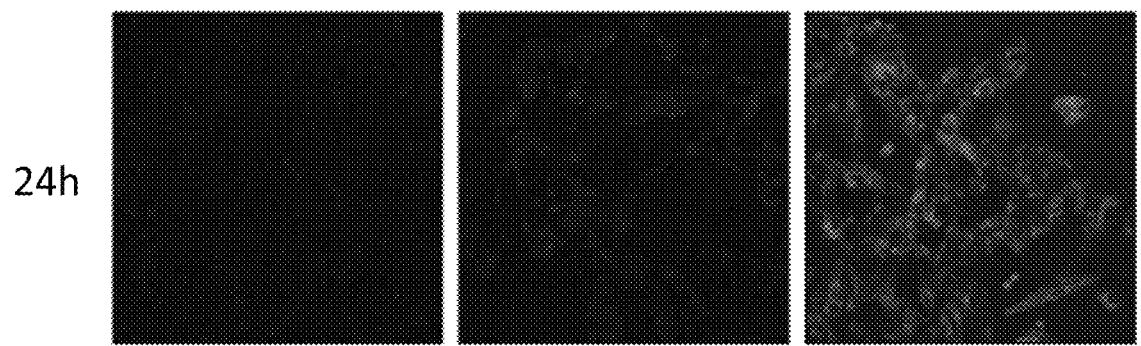

Exemplary HBM-coated nanoparticle composites were examined to determine if the membrane composition could be modified to influence site-directed delivery of an exemplary cancer therapeutic, such as Paclitaxel. As illustrated in FIGS. 31-33, selection of specific membrane components for incorporation into the HBM-coated nanoparticle composites can influence the activity of the composites. For example, FIG. 31 shows that the hydrodynamic radius of gold nanoparticles can be modified by tuning the membrane composition of the composite using different membrane components 1202-1208. These HBM-coated nanoparticle composites also exhibit good stability under different physiological salt concentrations as illustrated in FIG. 32. Different salt concentrations, such as 50 mM (bars "a" in FIG. 32), 150 mM (bars "b" in FIG. 32), and 200 mM (bars "c" in FIG. 32), were examined. Without being limited to a particular theory, it is currently believed that the reduced stability observed at 50 mM may be attributed to nanoparticle aggregation under high salt concentrations. Gold nanoparticle composites with Paclitaxel illustrated the least stability (bars "a," "b," and "c" for 1210). The HBM-coated nanoparticle composites also are stable a pH values ranging from 5-8, with some embodiments showing less stability at pH 2, as illustrated by FIG. 33 (wherein bars "a" represent results at pH 5 and bars "b" represent results at pH 2). Cyanide etch studies also were conducted to evaluate the effects of cyanide in combination with membrane disrupting agents (e.g., CHAPS, SDS, TritonX100, and Tween®20) on the nanoparticle stability. As illustrated by FIG. 34, the UV-vis spectra of HBM-coated gold nanoparticle composites show minimal changes in optical density and shift in the surface plasmon resonance (SPR) upon exposure to KCN and different membrane disrupting agents, thus indicating that the membrane remains intact even when membrane disrupting agents are present.

Example 11

Figure 36A:
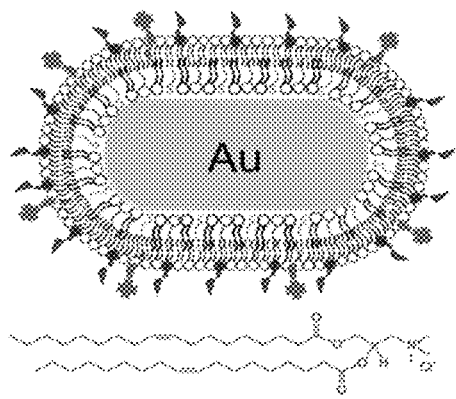
FIGS. 36A-36G show a representative nanoparticle composite comprising cationic groups (FIG. 36A) and confocal microscopy images (FIGS. 36B-36G) showing results obtained from analyzing the uptake of hybrid lipid-coated nanoparticle composites comprising rhodamine dyes and cationic molecules, such as N-[1-(2,3-Dioleoyloxy)propyl]-N,N,N-trimethylammonium chloride ("DOTAP") or cetyl trimethyl ammonium bromide ("CTAB"), which change the charge of the nanoparticles to make them more cationic to enhance cellular uptake; the results illustrate that the nanoparticle composites can readily be taken up in cells and that uptake can be dependent on the surface charge.
Figure 36B:
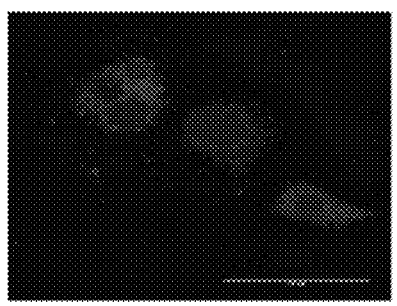
Figure 36C:
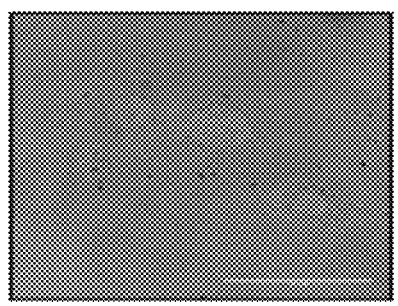
Figure 36D:
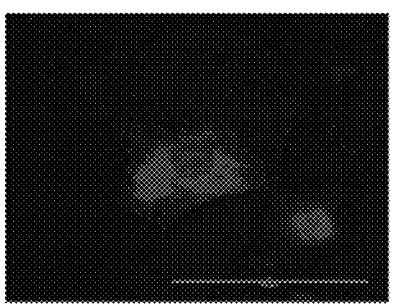
Figure 36E:
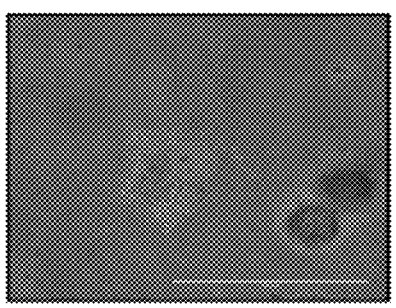
Figure 36F:
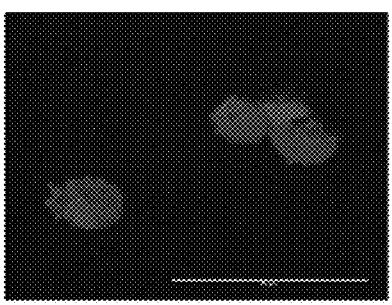
Figure 36G:
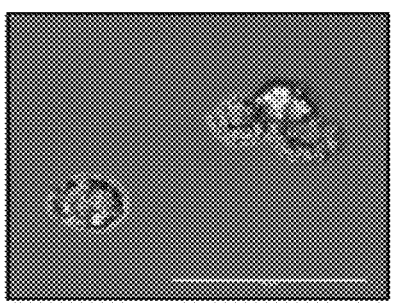

In this example, confocal microscopy was used to evaluate the uptake of hybrid lipid-coated gold nanoparticle composites labeled with rhodamine dyes. As illustrated by FIGS. 35A-35F, dye-labeled nanoparticle composites were observed in BHK cells at $10^5$ and $10^6$ nps/mL within four hours and no cell death was observed. This example confirms that the nanoparticle composites described herein are non-toxic and can readily be taken up in cells. In another embodiment, the uptake of hybrid lipid-coated nanoparticle composites comprising rhodamine dyes and cationic molecules, such as DOTAP and CTAB, was evaluated. As shown by FIGS. 36B-36E, the nanoparticle composites comprising cationic species, such as the nanoparticle composite illustrated in FIG. 36A, are readily taken up in cells in various concentrations (e.g., $4.1 \times 10^{10}$ nps/mL as shown by FIGS. 36B and 25C; $8.3 \times 10^{10}$ nps/mL as shown by FIGS. 36D and 36E; and $4.1 \times 10^{11}$ nps/mL as shown by FIGS. 36F and 36G).

VII. Overview of Several Embodiments

Disclosed herein are embodiments of a nanoparticle composite, comprising (i) one or more lipid molecules; (ii) one or more aggregation inhibitors; (iii) one or more stabilizing agents; and (iv) a nanoparticle core, comprising iron, silver, gadolinium, or an oxide thereof. In some embodiments, the nanoparticle core is covalently coupled to one or more stabilizing agent molecules through a heteroatom group of the one or more stabilizing agent molecules, the one or more stabilizing agent molecules further comprising an aliphatic chain.

In some embodiments, the nanoparticle composite comprises a nanoparticle core comprising silver, gold, gadolinium oxide, or iron oxide; and a hybrid lipid bilayer, comprising an stabilizing agent group comprising an aliphatic chain and a heteroatom terminus covalently bound to a surface of the nanoparticle core, wherein the heteroatom is nitrogen, oxygen, or sulfur; one or more lipids; and one or more aggregation inhibitors comprising a hydrophobic chain and a polar terminus that is not covalently attached to the surface of the nanoparticle core; and wherein when the nanoparticle core comprises gold, the stabilizing agent molecule is not, or is other than, propanethiol, hexanethiol, or decanethiol.

In any or all of the above embodiments, the one or more aggregation inhibitors comprises (i) a hydrophobic chain and (ii) a polar terminus that is not covalently attached to the surface of the nanoparticle core.

In any or all of the above embodiments, the one or more aggregation inhibitors and the one or more lipids can have the same structure.

In any or all of the above embodiments, the hydrophobic chain comprises two to 20 carbon atoms.

In any or all of the above embodiments, the polar terminus comprises a carboxylate group, a tetra-substituted ammonium group, a phosphate group, or a combination thereof.

In any or all of the above embodiments, the nanoparticle core has a spherical shape, an ellipsoidal shape, a rod-like shape, or a triangular shape.

In some embodiments, the nanoparticle core comprises iron oxide or gadolinium oxide and the stabilizing agent molecule comprises one or more oxygen atoms covalently attached to the iron oxide or gadolinium oxide.

In yet some other embodiments, the nanoparticle core comprises silver and the stabilizing agent molecule comprises a nitrogen atom covalently attached to the nanoparticle core.

In any or all of the above embodiments, the one or more aggregation inhibitors is oleic acid, oleate, or a mixture thereof; or L-α-phosphatidylcholine.

In any or all of the above embodiments, the composite can further comprise a plurality of the one or more aggregation inhibitors or a plurality of the one or more lipids that form a membrane surrounding the nanoparticle core.

In any or all of the above embodiments, the one or more lipid molecules, the one or more aggregation inhibitors, and the one or more stabilizing agents forms a hybrid lipid bilayer membrane that surrounds the nanoparticle core.

In any or all of the above embodiments, the composite further comprises one or more associated drugs, imaging agents, targeting agents, or a combination thereof.

In any or all of the above embodiments, the one or more associated drugs are anti-cancer drugs.

In any or all of the above embodiments, the one or more associated drugs are associated to the nanoparticle composite with a thioester linkage capable of being cleaved with a reactive oxygen species and/or an esterase enzyme.

In any or all of the above embodiments, the imaging agents are selected from chromogens, fluorophores, or mixtures thereof.

In any or all of the above embodiments, the chromogen or fluorophore emits a visible signal upon change in pH of the environment surrounding the nanoparticle composite.

In any or all of the above embodiments, the targeting agents are antibodies, peptides, folic acid, or sugar residues.

In any or all of the above embodiments, the nanoparticle core comprises iron oxide and/or gadolinium oxide and the one or more stabilizing agent molecules are siloxane-containing stabilizing agents comprising an aliphatic chain having from 6 to 20 carbon atoms, wherein oxygen atoms of the siloxane-containing stabilizing agent molecules are covalently coupled to the nanoparticle core.

In any or all of the above embodiments, the nanoparticle core comprises silver and the one or more stabilizing agent molecules comprises a nitrogen heteroatom group and an aliphatic chain having from 6 to 20 carbon atoms, wherein of the nitrogen heteroatom group is covalently coupled to the nanoparticle core.

Also disclosed herein are embodiments of a method of making the composite, comprising exposing the nanoparticle core to one or more aggregation inhibitors; exposing the nanoparticle core to one or more lipids; exposing the nanoparticle core to the stabilizing agent molecule; and isolating the composite.

In some embodiments, the method further comprises pre-determining the number of stabilizing agent molecules to be covalently attached to the nanoparticle core to thereby control the number of aggregation inhibitors needed to substantially cover the nanoparticle core.

In some embodiments, the method further comprises exposing the nanoparticle core to one or more surfactants to determine membrane integrity.

In any or all of the above method embodiments, pre-determining a number or proportion of stabilizing agent molecules, aggregation inhibitors, or combination thereof that will populate a surface of the nanoparticle core and/or reducing the number of lipid molecules (such as by matching the number of lipid molecules to the pre-determined number of stabilizing agent molecules, aggregation inhibitors, or combination thereof) used to make the composite and the excess lipid molecules (not part of a lipid-containing nanoparticle) contained in the reaction mixture after the surface is populated facilitates making a nanoparticle composite having a specific shape and prevents ion dissociation and/or nanoparticle composite degradation.

Also disclosed herein are embodiments of a method of using a nanoparticle composite. Such methods can comprise selecting a shape of a nanoparticle core component of the nanoparticle composite so as to influence a wavelength at which the nanoparticle composite will absorb energy; administering the nanoparticle composite to a subject; and detecting the presence of the nanoparticle composite in the subject using an energy source that produces energy at the wavelength at which the nanoparticle composite will absorb.

In some embodiments of such methods, the shape of the nanoparticle core component is selected to be a triangular shape so as to cause the nanoparticle composite to absorb at a wavelength longer than that of a spherical nanoparticle composite and/or an ellipsoidal nanoparticle composite.

In any or all of the above use embodiments, the shape of the nanoparticle core is not altered upon exposure to destabilizing agents and/or disruptive ions.

Also disclosed herein are uses of nanoparticle composites according to any one of the above embodiments in labeling and tracking macrophage subtypes in vivo or in vitro.

In view of the many possible embodiments to which the principles of the present disclosure may be applied, it should be recognized that the illustrated embodiments are only preferred examples of the disclosure and should not be taken as limiting the scope of the claimed invention. Rather, the scope is defined by the following claims. I therefore claim as my invention all that comes within the scope and spirit of these claims.

I claim:

1. A nanoparticle composite, comprising:
one or more lipid molecules that form a first layer of a hybrid membrane;
one or more aggregation inhibitors that have a different structure from the one or more lipid molecules;
one or more stabilizing agent molecules comprising a heteroatom group and an aliphatic chain comprising at least six carbon atoms, wherein the one or more aggregation inhibitors and the one or more stabilizing agent molecules form a second layer of the hybrid membrane; and
a nanoparticle core encapsulated by the hybrid membrane, wherein the nanoparticle core has a triangular shape and comprises silver or an oxide thereof; and wherein (i) the nanoparticle core is covalently coupled to the one or more stabilizing agent molecules through the heteroatom group of the one or more stabilizing agent molecules such that the second layer of the hybrid membrane surrounds the nanoparticle core and the first layer of the hybrid membrane surrounds the second layer of the hybrid membrane.

2. The nanoparticle composite of claim 1, wherein the one or more aggregation inhibitors comprises (i) a hydrophobic chain and (ii) a polar terminus that is not covalently attached to the surface of the nanoparticle core.

3. The nanoparticle composite of claim 2, wherein the hydrophobic chain comprises two to 20 carbon atoms.

4. The nanoparticle composite of claim 2, wherein the polar terminus comprises a carboxylate group, a tetra-substituted ammonium group, a phosphate group, or a combination thereof.

5. The nanoparticle composite of claim 1, wherein the one or more aggregation inhibitors is oleic acid, oleate, or a mixture thereof; or L-α-phosphatidylcholine.

6. The nanoparticle composite of claim 1, further comprising one or more associated drugs, imaging agents, targeting agents, or a combination thereof.

7. The nanoparticle composite of claim 6, wherein the one or more associated drugs are anti-cancer drugs.

8. The nanoparticle composite of claim 6, wherein the one or more associated drugs are associated to the nanoparticle composite with a thioester linkage capable of being cleaved with a reactive oxygen species and/or an esterase enzyme.

9. The nanoparticle composite of claim 6, wherein the imaging agents are selected from chromogens, fluorophores, or mixtures thereof.

10. The nanoparticle composite of claim 9, wherein the chromogen or fluorophore emits a visible signal upon change in pH of the environment surrounding the nanoparticle composite.

11. The nanoparticle composite of claim 6, wherein the targeting agents are antibodies, peptides, folic acid, or sugar residues.

12. The nanoparticle composite of claim 1, wherein the nanoparticle core comprises silver and the one or more stabilizing agent molecules comprises a nitrogen heteroatom group and an aliphatic chain having from 6 to 20 carbon atoms, wherein of the nitrogen heteroatom group is covalently coupled to the nanoparticle core.

13. A method of using the nanoparticle composite of claim 1, comprising:
  administering the nanoparticle composite to a subject or a sample; and
  detecting the presence of the nanoparticle composite in the subject or the sample using an energy source that produces energy at a wavelength at which the nanoparticle composite will absorb.

14. The method of claim 13, wherein the triangular shape of the nanoparticle core causes the nanoparticle composite to absorb at a wavelength longer than that of a spherical nanoparticle composite and/or an ellipsoidal nanoparticle composite.

15. The method of claim 13, wherein the triangular shape of the nanoparticle core is not altered upon exposure to destabilizing agents and/or disruptive ions.

16. The method of claim 13, wherein the nanoparticle composite labels and tracks macrophage subtypes in vivo or in vitro.

17. The nanoparticle composite of claim 1, wherein the nanoparticle core comprises silver and the one or more stabilizing agent molecules comprises a sulfur heteroatom group and an aliphatic chain having from 6 to 20 carbon atoms, wherein of the sulfur heteroatom group is covalently coupled to the nanoparticle core.

* * * * *